(12) United States Patent
Bose et al.

(10) Patent No.: US 12,089,980 B2
(45) Date of Patent: *Sep. 17, 2024

(54) SYSTEM AND METHOD FOR COUCH SAG COMPENSATION

(71) Applicant: SHANGHAI UNITED IMAGING HEALTHCARE CO., LTD., Shanghai (CN)

(72) Inventors: Supratik Bose, Houston, TX (US); Jonathan Maltz, Houston, TX (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 18/333,534

(22) Filed: Jun. 12, 2023

(65) Prior Publication Data

US 2023/0309945 A1 Oct. 5, 2023

Related U.S. Application Data

(63) Continuation of application No. 17/443,335, filed on Jul. 26, 2021, now Pat. No. 11,672,501, which is a (Continued)

(51) Int. Cl.
*A61B 6/00* (2024.01)
*A61B 5/055* (2006.01)
(Continued)

(52) U.S. Cl.
CPC ............ *A61B 6/5276* (2013.01); *A61B 5/055* (2013.01); *A61B 6/0492* (2013.01);
(Continued)

(58) Field of Classification Search
CPC ....................... A61B 6/5276; A61N 2005/1057
See application file for complete search history.

(56) References Cited

U.S. PATENT DOCUMENTS

| 5,872,829 A | 2/1999 | Wischmann et al. |
| 6,895,105 B2 | 5/2005 | Wollenweber |

(Continued)

FOREIGN PATENT DOCUMENTS

| CN | 104021547 A | 9/2014 |
| CN | 104680486 A | 6/2015 |

(Continued)

OTHER PUBLICATIONS

International Search Report in PCT/CN2018/075816 mailed on Nov. 5, 2018, 3 pages.

(Continued)

*Primary Examiner* — Vincent Rudolph
*Assistant Examiner* — Raphael Schwartz
(74) *Attorney, Agent, or Firm* — METIS IP LLC

(57) ABSTRACT

The method may include obtaining a first set of imaging data affording a sagittal view relating to a subject and a first couch supporting the subject. The first couch may have a plurality of first positions reflected in the first set of imaging data as a first conformation. The method may also include determining a displacement field associated with a first set of imaging data with respect to the reference conformation based on the first conformation and a reference conformation. The method may further include adjusting the first set of imaging data with respect to the reference conformation based on the displacement field. In some embodiments, the method may include obtaining an image of the subject with respect to the reference conformation based on the adjusted first set of imaging data.

20 Claims, 12 Drawing Sheets

Related U.S. Application Data continuation of application No. 16/194,243, filed on Nov. 16, 2018, now Pat. No. 11,071,510, which is a continuation of application No. PCT/CN2018/075816, filed on Feb. 8, 2018.

(51) Int. Cl.
*A61B 6/03* (2006.01)
*A61B 6/04* (2006.01)
*A61B 6/42* (2024.01)
*G06T 7/00* (2017.01)
*G06T 7/73* (2017.01)
*G06T 11/00* (2006.01)

(52) U.S. Cl.
CPC .......... *A61B 6/5235* (2013.01); *G06T 7/0012* (2013.01); *G06T 7/0014* (2013.01); *G06T 7/73* (2017.01); *A61B 6/032* (2013.01); *A61B 6/4258* (2013.01); *A61B 6/5205* (2013.01); *G06T 11/005* (2013.01); *G06T 11/008* (2013.01); *G06T 2207/10072* (2013.01)

(56) References Cited

U.S. PATENT DOCUMENTS

| | | | |
|---|---|---|---|
| 7,020,315 | B2 | 3/2006 | Vaisburd et al. |
| 7,607,833 | B2 | 10/2009 | Märzendorfer |
| 8,086,010 | B2 | 12/2011 | Nabatame et al. |
| 8,107,730 | B2 | 1/2012 | Kariv |
| 8,511,894 | B2 | 8/2013 | Gagnon et al. |
| 8,983,161 | B2 | 3/2015 | Berkus et al. |
| 2002/0186819 | A1 | 12/2002 | Proksa |
| 2007/0003020 | A1* | 1/2007 | Hsieh ............... A61B 6/037 378/207 |
| 2007/0074347 | A1 | 4/2007 | Coppens et al. |
| 2008/0031414 | A1 | 2/2008 | Coppens |
| 2008/0123924 | A1* | 5/2008 | Nabatame ........... A61B 6/0487 382/131 |
| 2011/0301449 | A1 | 12/2011 | Maurer, Jr. |
| 2014/0016759 | A1 | 1/2014 | Ngar et al. |
| 2015/0154756 | A1 | 6/2015 | Gerganov et al. |
| 2016/0110893 | A1 | 4/2016 | Pang et al. |
| 2016/0143607 | A1* | 5/2016 | Cao ................. A61B 6/027 378/20 |
| 2017/0112416 | A1 | 4/2017 | Hao et al. |
| 2017/0243336 | A1 | 8/2017 | Zou et al. |
| 2018/0339172 | A1 | 11/2018 | Stahl et al. |

FOREIGN PATENT DOCUMENTS

| | | |
|---|---|---|
| CN | 107049352 A | 8/2017 |
| GB | 2312115 A | 10/1997 |
| WO | 2007035920 A2 | 3/2007 |

OTHER PUBLICATIONS

Written Opinion in PCT/CN2018/075816 mailed on Nov. 5, 2018, 3 pages.

Jean-Sébastien Affagard et al., Use of Digital Image Correlation and Ultrasound: Analysis of Thigh Muscle Displacement Fields, IEEE 2015 37th Annual International Conference of the IEEE Engineering in Medicine and Biology Society, 3827-3830, 2015.

* cited by examiner

600

```
┌─────────────────────────────────────────────────────────┐
│ Obtaining a first set of imaging data affording a       │  602
│ sagittal view relating to a subject and a couch         │
│ supporting the subject, the couch having a plurality    │
│ of first positions reflected in the first set of        │
│ imaging data as a first conformation                    │
└─────────────────────────────────────────────────────────┘
                            │
                            ▼
┌─────────────────────────────────────────────────────────┐
│ Determining a displacement field associated with the    │  604
│ first set of imaging data with respect to the reference │
│ conformation based on the first conformation and a      │
│ reference conformation                                  │
└─────────────────────────────────────────────────────────┘
                            │
                            ▼
┌─────────────────────────────────────────────────────────┐
│ Adjusting the first set of imaging data with respect    │  606
│ to the reference conformation based on the              │
│ displacement field                                      │
└─────────────────────────────────────────────────────────┘
                            │
                            ▼
┌─────────────────────────────────────────────────────────┐
│ Obtaining an image of the subject with respect to the   │  608
│ reference conformation based on the adjusted first      │
│ set of imaging data                                     │
└─────────────────────────────────────────────────────────┘
```

```
┌─────────────────────────────────────────────────────────┐
│ Obtaining a first image slice affording a sagittal view │
│ relating to a region of interest (ROI) of a subject and │   702
│ a first couch supporting the subject, the first couch   │
│ having a plurality of first positions reflected in the  │
│ first image slice as a first conformation, the first    │
│ image slice corresponding to a stack of third image     │
│ slices affording axial views                            │
└─────────────────────────────────────────────────────────┘
                            │
                            ▼
┌─────────────────────────────────────────────────────────┐
│ Obtaining a second image slice affording the sagittal   │
│ view relating to the ROI of the subject and a second    │   704
│ couch supporting the subject, the second couch having   │
│ a plurality of second positions reflected in the second │
│ image slice as a second conformation                    │
└─────────────────────────────────────────────────────────┘
                            │
                            ▼
┌─────────────────────────────────────────────────────────┐
│ Determining a displacement field associated with the    │
│ first image slice based on the first conformation and   │   706
│ the second conformation, the displacement field         │
│ including a plurality of displacement components        │
└─────────────────────────────────────────────────────────┘
                            │
                            ▼
┌─────────────────────────────────────────────────────────┐
│ Adjusting the first stack of image slices based on the  │   708
│ displacement field                                      │
└─────────────────────────────────────────────────────────┘
```

┌─────────────────────────────────────────────────────────┐
│ Obtaining a first stack of image slices affording axial views │ 1002
│ relating to an ROI of the subject and a first couch supporting the │
│ subject, the first couch having a plurality of first positions │
│ reflected in the first stack of image slices as a first conformation │
└─────────────────────────────────────────────────────────┘
                            ↓
┌─────────────────────────────────────────────────────────┐
│ Obtaining a second stack of image slices affording the axial │ 1004
│ views relating to the ROI of the subject and a second couch │
│ supporting the subject, the second couch having a plurality of │
│ second positions reflected in the second stack of image slices │
│ as a second conformation │
└─────────────────────────────────────────────────────────┘
                            ↓
┌─────────────────────────────────────────────────────────┐
│ Determining a displacement field associated with associated │ 1006
│ with the first stack of image slices based on the first │
│ conformation and the second conformation, the displacement │
│ field including a plurality of displacement components, each │
│ image slice of the first stack corresponding to one displacement │
│ component of the plurality of displacement components │
└─────────────────────────────────────────────────────────┘
                            ↓
┌─────────────────────────────────────────────────────────┐
│ Adjusting the first stack of image slices based on the │ 1008
│ displacement field │
└─────────────────────────────────────────────────────────┘

FIG. 10

SYSTEM AND METHOD FOR COUCH SAG COMPENSATION

CROSS REFERENCE TO RELATED APPLICATIONS

This present application is a continuation of U.S. application Ser. No. 17/443,335, filed on Jul. 26, 2021, which is a continuation of U.S. application Ser. No. 16/194,243, filed on Nov. 16, 2018, now patent Ser. No. 11/071,510, which is a continuation of International Application No. PCT/CN2018/075816 filed on Feb. 8, 2018, the entire contents of which are incorporated herein by reference.

TECHNICAL FIELD

The present disclosure generally relates to a medical system, and more particularly, to a system and method for couch sag compensation in a medical or imaging procedure.

BACKGROUND

Various imaging techniques have been widely used in medical diagnosis, radiation therapy planning, surgery planning and other medical procedures, such as X-ray imaging, magnetic resonance imaging (MRI), computed tomography (CT), positron emission tomography (PET), etc. Generally, a couch may be used to support and/or transfer a subject to be examined to a scanning region of an imaging device and/or a treatment device. In some embodiments, a couch loaded with the subject (e.g., a patient) may deform (or referred to as sag or deflect) in a medical procedure. For example, in a multi-modality imaging, the couch may sag when the couch is extended along the longitudinal direction of the couch to scanning regions of the multi-modality imaging device, causing mismatch of images taken at different positions. As another example, in an imaging guided radiation therapy (IGRT) procedure, the couch may sag, warp, or rotate when the couch is moved from an imaging device to a treatment device, causing inaccurate positioning of a target point (e.g., an anatomical point). Thus, it may be desirable to develop a method or a system to compensate the sag of a couch.

SUMMARY

According to an aspect of the present disclosure, a method for couch sag compensation in a medical or imaging procedure is provided. The method may include obtaining a first set of imaging data affording a sagittal view relating to a subject and a first couch supporting the subject. The first couch may have a plurality of first positions reflected in the first set of imaging data as a first conformation. The method may also include determining, based on the first conformation and a reference conformation, a displacement field associated with the first set of imaging data with respect to the reference conformation. The method may also include adjusting, based on the displacement field, the first set of imaging data with respect to the reference conformation. The method may also include obtaining, based on the adjusted first set of imaging data, an image of the subject with respect to the reference conformation.

In some embodiments, for one first position of the first couch, the method may further include determining a corrected first point on the reference conformation corresponding to a first point of the first set of imaging data on the first conformation. The first point may correspond to the one first position of the first couch. The method may also include determining a displacement component associated with the first point. A first distance between the corrected first point and an intersection may equal a second distance between the first point and the intersection between the reference conformation and the first conformation. The displacement component of the first point may be determined as a vector from the first point to the corrected first point.

In some embodiments, the displacement component of the first point may include a third distance from the first point to the corrected first point, and a direction from the first point to the corrected first point.

In some embodiments, distances between various first points the intersection may change as a function of corresponding first positions nonlinearly.

In some embodiments, the method may further include determining a displacement component of a second point of the first set of imaging data on the first conformation. The second point may be different from the first point. A direction of a vector associated with the second point may be different from the direction of the vector associated with the first point.

In some embodiments, the method may further include adjusting imaging data in an axial view corresponding to the first point in the sagittal view based on the displacement component corresponding to the first point.

In some embodiments, the method may further include generating an adjusted 3D image or an adjusted 2D image slice in a view other than the axial view based on the adjusted imaging data.

In some embodiments, the method may further include moving, based on the displacement field, spatial basis function representations corresponding to the first set of imaging data.

In some embodiments, the displacement field may include a plurality of rotation angles, and the plurality of rotation angles may relate to spatial basis function representations corresponding to the first set of imaging data.

In some embodiments, at least two rotation angles corresponding to different spatial basis function representations may be different.

In some embodiments, the method may further include determining a reference position of the first couch reflected in the first set of imaging data. The first conformation of the first couch may coincide with the reference conformation at the reference position. The reference position may correspond to a reference spatial basis function representation.

In some embodiments, the rotation angle corresponding to a spatial basis function representation may relate to a distance between the spatial basis function representation and the reference spatial basis function representation.

In some embodiments, the reference conformation may include a straight horizontal line.

In some embodiments, the reference conformation may correspond to a plurality of second positions reflected in a second set of imaging data.

In some embodiments, the second set of imaging data may afford a sagittal view relating to the subject and a second couch supporting the subject. The plurality of second positions may correspond to the second couch.

According to another aspect of the present disclosure, a method for couch sag compensation in a medical or imaging procedure is provided. The method may include obtaining a first image slice affording a sagittal view relating to a region of interest (ROI) of a subject and a first couch supporting the subject. The first couch may have a plurality of first positions reflected in the first image slice as a first conformation. The first image slice may correspond to a stack of third image slices affording axial views. The method may also include obtaining a second image slice affording a sagittal view relating to the ROI of the subject and a second couch supporting the subject. The second couch may have a plurality of second positions reflected in the second image slice as a second conformation. The method may also include determining, based on the first conformation and the second conformation, a displacement field associated with the first image slice with respect to the second image slice. The displacement field may include a plurality of displacement components. Each third image slice of the stack may correspond to one displacement component of the plurality of displacement components. The method may also include adjusting, based on the displacement field, at least one third image slice.

In some embodiments, the method may further include, for a third image slice of the stack, moving, based on a corresponding displacement component of the displacement field, a plurality of pixels in the third image slice.

In some embodiments, the method may further include moving, based on the displacement field, spatial basis function representations corresponding to the imaging data.

In some embodiments, the first image slice may be acquired by a first device and the second image slice may be acquired by a second device different from the first device.

In some embodiments, the first device may include an imaging device including at least one of a computed tomography (CT) scanner, a positron emission tomography (PET) scanner, a single photon emission computed tomography (SPECT) scanner, or a magnetic resonance (MR) scanner.

In some embodiments, the first device further may include an interventional medical device, including at least one of a radiation therapy (RT) treatment system, an ultrasound treatment system, a thermal treatment system, or a surgical intervention system.

In some embodiments, the first image slice may include at least a pixel or spatial basis function representation corresponding to an isocenter of the first device, and the second image slice may include at least a pixel or spatial basis function representation corresponding to an isocenter of the second device.

In some embodiments, the method may further include determining, based on the first conformation and the second conformation, each displacement component of the plurality of displacement components.

In some embodiments, the method may further include determining a reference position of the second couch reflected in the second image slice or the first couch reflected in the first image slice. The reference position may correspond to an intersection between the first conformation of the first couch and the second conformation of the second couch determined by registering the first image slice and the second image slice. The method may also include, for each first position of the first couch, determining a first length of a portion of the first couch between the reference position and the first position reflected in the first image slice. The method may also include determining, based on the first length, the displacement component corresponding to the first position.

In some embodiments, the method may further include determining, based on the first length, a second length between the reference position and a corrected first position of the first couch with respect to the second conformation of the second couch. The method may also include determining, based on the first length and the second length, the displacement component corresponding to the first position.

In some embodiments, the second length may be equal to the first length.

In some embodiments, the second length may relate to an elastic extension of the first couch between the reference position and the first position.

In some embodiments, the method may further include determining, based on the first position of the first couch and a corresponding second position of the second couch reflected in the second image slice, a first deformation element in a vertical direction at the first position of the first conformation with respect to the second conformation. The method may also include determining a first distance in a horizontal direction between the reference position and the first position. The method may also include determining, based on the first deformation element in the vertical direction and the first distance in the horizontal direction, the first length.

In some embodiments, the method may further include determining the rotation angle associated with the first position based on the first length, the first deformation element in the vertical direction, and the first distance in the horizontal direction.

In some embodiments, the method may further include, for each pair of adjacent positions between the reference position and the first position of the first couch reflected in the first image slice, determining a section length of a section of the first conformation between the each pair of adjacent positions reflected in the first image slice. The method may also include obtaining the first length by summing the section lengths.

In some embodiments, the method may further include determining a reference position of the second couch reflected in the second image slice or the first couch reflected in the first image slice. The reference position may correspond to an intersection between the first conformation of the first couch and the second conformation of the second couch determined by registering the first image slice and the second image slice. The method may also include, for each second position of the second couch, determining, based on the second position of the second couch and a corresponding first position of the first couch reflected in the first image slice, a second deformation element in a vertical direction of the first conformation with respect to the second conformation. The method may also include determining a second distance in a horizontal direction between the reference position and the first position reflected in the first image slice. The method may also include determining, based on the second deformation element in the vertical direction and the second distance in the horizontal direction, the rotation angle associated with the first position.

According to another aspect of the present disclosure, a method for couch sag compensation in a medical or imaging procedure is provided. The method may include obtaining a first image slice in a first view relating to a subject or a region of interest (ROI) of the subject and a first conformation. The first image slice may correspond to a stack of second image slices in a second view. The method may also include determining, based on the first conformation and a reference conformation, a displacement field associated with the first image slice with respect to the reference conformation, the displacement field including a plurality of displacement components. Each second image slice of the stack may correspond to one displacement component of the plurality of displacement components.

In some embodiments, the method may further include adjusting, based on the displacement field, spatial basis function representations corresponding to imaging data. The imaging data may correspond to the stack of second image slices.

In some embodiments, the method may further include adjusting, based on the displacement field, the stack of second image slices.

In some embodiments, the method may further include, for a second image slice of the stack, moving, based on the corresponding displacement component of the displacement field, a plurality of pixels in the second image slice.

In some embodiments, the first conformation may correspond to a plurality of first positions of a first couch reflected in the first image slice, and the reference conformation may correspond to a plurality of second positions of a second couch reflected in a third image slice affording the first view.

In some embodiments, the first image slice may be acquired by a first device and the third image slice may be acquired by a second device different from the first device.

In some embodiments, the first device or the second device may include an imaging device including at least one of a computed tomography (CT) scanner, a positron emission tomography (PET) scanner, a single photon emission computed tomography (SPECT) scanner, or a magnetic resonance (MR) scanner.

In some embodiments, the first device or the second device may further include an interventional medical device, including a radiation therapy (RT) treatment system, an ultrasound treatment system, a thermal treatment system, or a surgical intervention system.

In some embodiments, the first image slice may include at least a pixel or a spatial basis function representation corresponding to an isocenter of the first device, and the third image slice may include at least a pixel or a spatial basis function representation corresponding to an isocenter of the second device.

In some embodiments, the method may further include registering, based on the displacement field, the stack of second image slices and a stack of fourth image slices affording the second view corresponding to the third image slice.

In some embodiments, the method may further include registering, based on a displacement component corresponding to a second image slice, a corresponding fourth image slice and the second image slice.

In some embodiments, a displacement component may include at least one of a rotation element or a translation element.

In some embodiments, the first view may be perpendicular to the second view.

According to another aspect of the present disclosure, a system may include a storage device storing a set of instructions and one or more processors in communication with the storage device. When executing the instructions, one or more processors may be configured to cause the system to obtain a first set of imaging data affording a sagittal view relating to a subject and a first couch supporting the subject. The first couch may have a plurality of first positions reflected in the first set of imaging data as a first conformation. The one or more processors may also determine, based on the first conformation and a reference conformation, a displacement field associated with the first set of imaging data with respect to the reference conformation. The one or more processors may also adjust, based on the displacement field, the first set of imaging data with respect to the reference conformation. The one or more processors may also obtain, based on the adjusted first set of imaging data, an image of the subject with respect to the reference conformation.

According to another aspect of the present disclosure, a system for couch sag compensation in a medical or imaging procedure is provided. The system may include a storage device storing a set of instructions and one or more processors in communication with the storage device. When executing the instructions, one or more processors may be configured to cause the system to obtain a first image slice affording a sagittal view relating to a region of interest (ROI) of a subject and a first couch supporting the subject. The first couch may have a plurality of first positions reflected in the first image slice as a first conformation. The first image slice may correspond to a stack of third image slices affording axial views. The one or more processors may also obtain a second image slice affording a sagittal view relating to the ROI of the subject and a second couch supporting the subject. The second couch may have a plurality of second positions reflected in the second image slice as a second conformation. The one or more processors may also determine, based on the first conformation and the second conformation, a displacement field associated with the first image slice with respect to the second image slice. The displacement field may include a plurality of displacement components. Each third image slice of the stack may correspond to one displacement component of the plurality of displacement components. The one or more processors may also adjust, based on the displacement field, at least one third image slice.

According to another aspect of the present disclosure, a system for couch sag compensation in a medical or imaging procedure is provided. The system may include a storage device storing a set of instructions and one or more processors in communication with the storage device. When executing the instructions, one or more processors may be configured to cause the system to obtain a first image slice in a first view relating to a subject or a region of interest (ROI) of the subject and a first conformation. The first image slice may correspond to a stack of second image slices in a second view. The one or more processors may also determine, based on the first conformation and a reference conformation, a displacement field associated with the first image slice with respect to the reference conformation, the displacement field including a plurality of displacement components. Each second image slice of the stack may correspond to one displacement component of the plurality of displacement components.

According to another aspect of the present disclosure, a non-transitory computer readable medium may include instructions. When executed by at least one processor, the executions may cause the at least one processor to implement a method. The method may include obtaining a first set of imaging data affording a sagittal view relating to a subject and a first couch supporting the subject. The first couch may have a plurality of first positions reflected in the first set of imaging data as a first conformation. The method may also include determining, based on the first conformation and a reference conformation, a displacement field associated with the first set of imaging data with respect to the reference conformation. The method may also include adjusting, based on the displacement field, the first set of imaging data with respect to the reference conformation. The method may also include obtaining, based on the adjusted first set of imaging data, an image of the subject with respect to the reference conformation.

According to another aspect of the present disclosure, a non-transitory computer readable medium may include instructions. When executed by at least one processor. The executions may cause the at least one processor to implement a method. The method may include obtaining a first image slice affording a sagittal view relating to a region of interest (ROI) of a subject and a first couch supporting the subject. The first couch may have a plurality of first positions reflected in the first image slice as a first conformation. The first image slice may correspond to a stack of third image slices affording axial views. The method may also include obtaining a second image slice affording a sagittal view relating to the ROI of the subject and a second couch supporting the subject. The second couch may have a plurality of second positions reflected in the second image slice as a second conformation. The method may also include determining, based on the first conformation and the second conformation, a displacement field associated with the first image slice with respect to the second image slice. The displacement field may include a plurality of displacement components. Each third image slice of the stack may correspond to one displacement component of the plurality of displacement components. The method may also include adjusting, based on the displacement field, at least one third image slice.

According to another aspect of the present disclosure, a non-transitory computer readable medium may include instructions. When executed by at least one processor. The executions may cause the at least one processor to implement a method. The method may include obtaining a first image slice in a first view relating to a subject or a region of interest (ROI) of the subject and a first conformation. The first image slice may correspond to a stack of second image slices in a second view. The method may also include determining, based on the first conformation and a reference conformation, a displacement field associated with the first image slice with respect to the reference conformation, the displacement field including a plurality of displacement components. Each second image slice of the stack may correspond to one displacement component of the plurality of displacement components.

According to another aspect of the present disclosure, a system having at least one processor and a storage device may include an image data acquisition module, a displacement determination module, and an image correction module. The image data acquisition module may be configured to obtain a first set of imaging data affording a sagittal view relating to a subject and a first couch supporting the subject. The first couch may have a plurality of first positions reflected in the first set of imaging data as a first conformation. The displacement determination module may be configured to determine, based on the first conformation and a reference conformation, a displacement field associated with the first set of imaging data with respect to the reference conformation. The image correction module may be configured to adjust, based on the displacement field, the first set of imaging data with respect to the reference conformation. The image correction module may be configured to obtain, based on the adjusted first set of imaging data, an image of the subject with respect to the reference conformation.

According to another aspect of the present disclosure, a system having at least one processor and a storage device may include an image data acquisition module, a displacement determination module, and an image correction module. The image data acquisition module may be configured to obtain a first image slice affording a sagittal view relating to a region of interest (ROI) of a subject, a first couch supporting the subject, a second image slice affording a sagittal view relating to the ROI of the subject and a second couch supporting the subject. The first couch may have a plurality of first positions reflected in the first image slice as a first conformation. The first image slice may correspond to a stack of third image slices affording axial views. The second couch may have a plurality of second positions reflected in the second image slice as a second conformation. The displacement determination module may be configured to determine, based on the first conformation and the second conformation, a displacement field associated with the first image slice with respect to the second image slice. The displacement field may include a plurality of displacement components. Each third image slice of the stack may correspond to one displacement component of the plurality of displacement components. The image correction module may be configured to adjust based on the displacement field, at least one third image slice.

According to another aspect of the present disclosure, a system having at least one processor and a storage device may include an image data acquisition module, and a displacement determination module. The image data acquisition module may be configured to obtain a first image slice in a first view relating to a subject or a region of interest (ROI) of the subject and a first conformation. The first image slice may correspond to a stack of second image slices in a second view. The displacement determination module may be configured to determine, based on the first conformation and a reference conformation, a displacement field associated with the first image slice with respect to the reference conformation. The displacement field may include a plurality of displacement components. Each second image slice of the stack may correspond to one displacement component of the plurality of displacement components.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 6 is a flowchart illustrating an exemplary process for correcting an image slice according to some embodiments of the present disclosure;

FIG. 7 is a flowchart illustrating an exemplary process for correcting an image slice according to some embodiments of the present disclosure;

FIG. 10 is a flowchart illustrating an exemplary process for correcting an image slice according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 3:
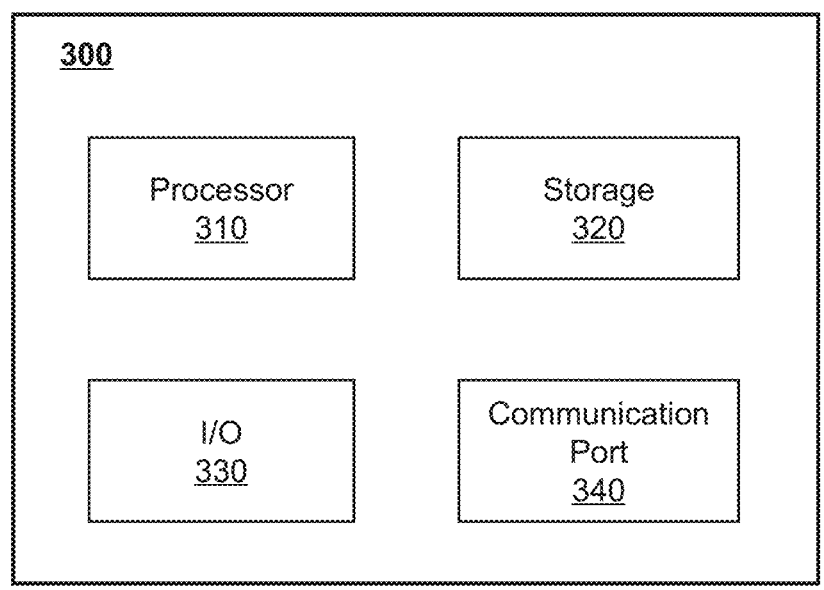
FIG. 3 is a schematic diagram illustrating exemplary hardware and/or software components of an exemplary computing device on which the processing engine may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Provided herein are systems and methods for medical diagnostic and/or treatment. In some embodiments, the medical system may include an diagnostic system. The diagnostic system may include a multi-modality imaging system. The multi-modality imaging system may include, for example, a computed tomography-positron emission tomography (CT-PET) system, a computed tomography-positron emission tomography-magnetic resonance imaging (CT-MRI) system, a X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a digital subtraction angiography-magnetic resonance imaging (DSA-MRI) system, or the like, or a combination thereof. In some embodiments, the medical system may include a diagnostic and treatment system. The diagnostic and treatment system may include a treatment plan system (TPS), an image-guide radio therapy (IGRT) system, etc. Merely by way of example, the image guided radio therapy (IGRT) system may include, for example, a CT guided radiotherapy system, an MRI guided radiotherapy system, etc.

The present disclosure relates to a system and method for couch sag compensation in a medical or imaging procedure. The method may include obtaining a first set of imaging data affording a sagittal view relating to a subject and a couch supporting the subject. The couch may have a plurality of first positions reflected in the first set of imaging data as a first conformation. The method may further include determining a displacement field associated with the first set of imaging data with respect to a reference conformation based on the first conformation and the reference conformation. The first set of imaging data with respect to the reference conformation may be adjusted based on the displacement field. Then, an image of the subject with respect to the reference conformation may be obtained based on the adjusted first set of imaging data.

It should be noted that the diagnostic and treatment system 100 described below is merely provided for illustration purposes, and not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
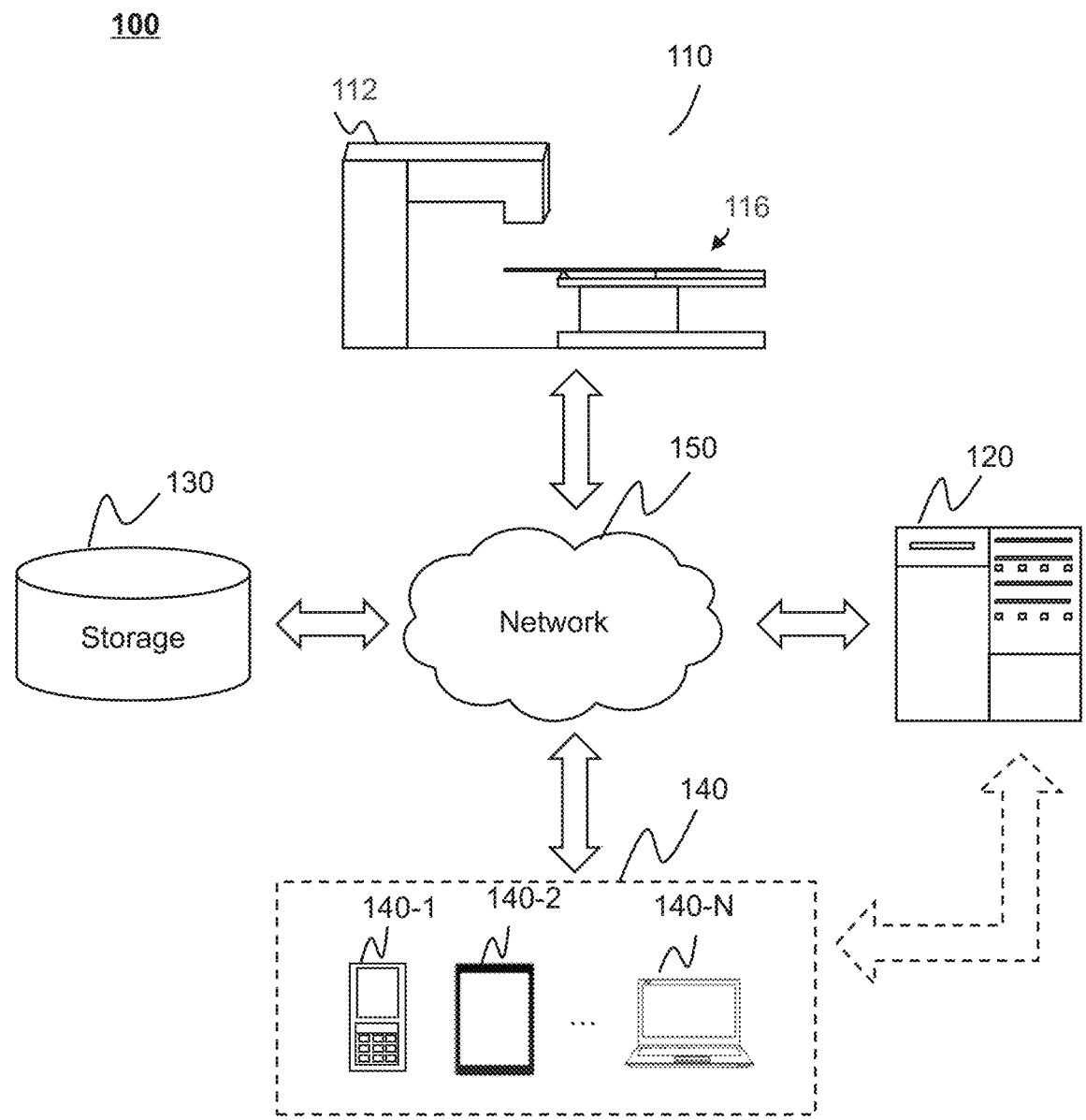
FIG. 1 is a schematic diagram illustrating an exemplary diagnostic and treatment system according to some embodiments of the present disclosure.

FIG. 1 is a schematic diagram illustrating an exemplary diagnostic and treatment system 100 according to some embodiments of the present disclosure. As shown, the diagnostic and treatment system 100 may include a medical apparatus 110, a processing device 120, storage 130, one or more terminal(s) 140, and a network 150. In some embodiments, the medical apparatus 110, the processing device 120, the storage 130, and/or the terminal(s) 140 may be connected to and/or communicate with each other via a wireless connection (e.g., the network 150), a wired connection, or any combination thereof. The connections between the components in the diagnostic and treatment system 100 may vary. Merely by way of example, the medical apparatus 110 may be connected to the processing device 120 through the network 150, as illustrated in FIG. 1. As another example, the medical apparatus 110 may be connected to the processing device 120 directly. As a further example, the storage 130 may be connected to the processing device 120 through the network 150, as illustrated in FIG. 1, or connected to the processing device 120 directly. As still a further example, the terminal(s) 140 may be connected to the processing device 120 through the network 150, as illustrated in FIG. 1, or connected to the processing device 120 directly.

The medical apparatus 110 may acquire imaging data relating to at least one part of a subject. The imaging data relating to at least one part of a subject may include an image (e.g., an image slice), projection data, or a combination thereof. In some embodiments, the imaging data may be a two-dimensional (2D) imaging data, a three-dimensional (3D) imaging data, a four-dimensional (4D) imaging data, or the like, or any combination thereof. In some embodiments, the imaging data may afford a sagittal view, an axial view, a coronal view, etc. The subject may be biological or non-biological. For example, the subject may include a patient, a man-made object, etc. As another example, the subject may include a specific portion, organ, and/or tissue of the patient. For example, the subject may include the head, the neck, the thorax, the heart, the stomach, a blood vessel, soft tissue, a tumor, nodules, or the like, or any combination thereof.

In some embodiments, the medical apparatus 110 may be a single-modality apparatus. For example, the medical apparatus 110 may include an imaging device 112. The imaging device 112 may be configured to provide the imaging data for determining the at least one part of the subject (e.g., an anatomical point). The imaging device 112 may include a CT device, a CBCT device, a PET device, a volume CT device, an MRI device, a SPECT device, or the like, or a combination thereof. The medical apparatus 110 may further include a couch 116. The couch 116 may be configured to support and/or transfer the at least one part of the subject to, for example, a scanning region of the imaging device 112.

In some embodiments, the medical apparatus 110 may be a multi-modality (e.g., two-modality) apparatus. For example, the imaging device 112 may include a CT-PET device, a CT-MRI device, a PET-MRI device, a SPECT-CT device, or the like, or a combination thereof. As another example, the medical apparatus 110 may further include an interventional medical device. Exemplary interventional medical devices may include a radiation therapy (RT) device, an ultrasound treatment device, a thermal treatment device, a surgical intervention device, or the like, or a combination thereof. In some embodiments, the imaging device 112 and the interventional medical device may be located separately from each other. In some embodiments, the imaging device 112 may be coupled with the interventional medical device. The imaging device 112 and the interventional medical device may share a same bore that may be used to accommodate a subject to be imaged and/or treated. More descriptions of the medical apparatus 110 may be found elsewhere in the present disclosure. See for example, FIG. 2 and the descriptions thereof.

The processing device 120 may process data and/or information obtained from the medical apparatus 110, the storage 130, and/or the terminal(s) 140. For example, the processing device 120 may determine a displacement field associated with a stack of image slices. The displacement field may include a plurality of displacement components. An image slice of the stack may correspond to one displacement component of the plurality of displacement components. As another example, the processing device 120 may adjust the stack of image slices based on the displacement field.

In some embodiments, the processing device 120 may be a single server or a server group. The server group may be centralized or distributed. In some embodiments, the processing device 120 may be local or remote. For example, the processing device 120 may access information and/or data from the medical apparatus 110, the storage 130, and/or the terminal(s) 140 via the network 150. As another example, the processing device 120 may be directly connected to the medical apparatus 110, the terminal(s) 140, and/or the storage 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented by a mobile device 400 having one or more components as described in connection with FIG. 4.

The storage 130 may store data, instructions, and/or any other information. In some embodiments, the storage 130 may store data obtained from the medical apparatus 110, the processing device 120, and/or the terminal(s) 140. In some embodiments, the storage 130 may store data and/or instructions that the processing device 120 may execute or use to perform exemplary methods described in the present disclosure. In some embodiments, the storage 130 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 130 may be implemented on a cloud platform as described elsewhere in the disclosure.

In some embodiments, the storage 130 may be connected to the network 150 to communicate with one or more other components in the diagnostic and treatment system 100 (e.g., the processing device 120, the terminal(s) 140, etc.). One or more components in the diagnostic and treatment system 100 may access the data or instructions stored in the storage 130 via the network 150. In some embodiments, the storage 130 may be part of the processing device 120.

The terminal(s) 140 may be connected to and/or communicate with the medical apparatus 110, the processing device 120, and/or the storage 130. For example, the terminal(s) 140 may obtain a processed image from the processing device 120. As another example, the terminal(s) 140 may obtain imaging data acquired via the medical apparatus 110 and transmit the imaging data to the processing device 120 to be processed. In some embodiments, the terminal(s) 140 may include a mobile device 140-1, a tablet computer 140-2, ... , a laptop computer 140-N, or the like, or any combination thereof. For example, the mobile device 140-1 may include a mobile phone, a personal digital assistant (PDA), a gaming device, a navigation device, a point of sale (POS) device, a laptop, a tablet computer, or the like, or any combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or any combination thereof. In some embodiments, the terminal(s) 140 may be part of the processing device 120.

The network 150 may include any suitable network that can facilitate exchange of information and/or data for the diagnostic and treatment system 100. In some embodiments, one or more components of the diagnostic and treatment system 100 (e.g., the medical apparatus 110, the processing device 120, the storage 130, the terminal(s) 140, etc.) may communicate information and/or data with one or more other components of the diagnostic and treatment system 100 via the network 150. For example, the processing device 120 may obtain imaging data from the medical apparatus 110 via the network 150. As another example, the processing device 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the diagnostic and treatment system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage 130 may be a data storage including cloud computing platforms, such as, public cloud, private cloud, community, and hybrid clouds, etc. However, those variations and modifications do not depart the scope of the present disclosure.

Figure 2:
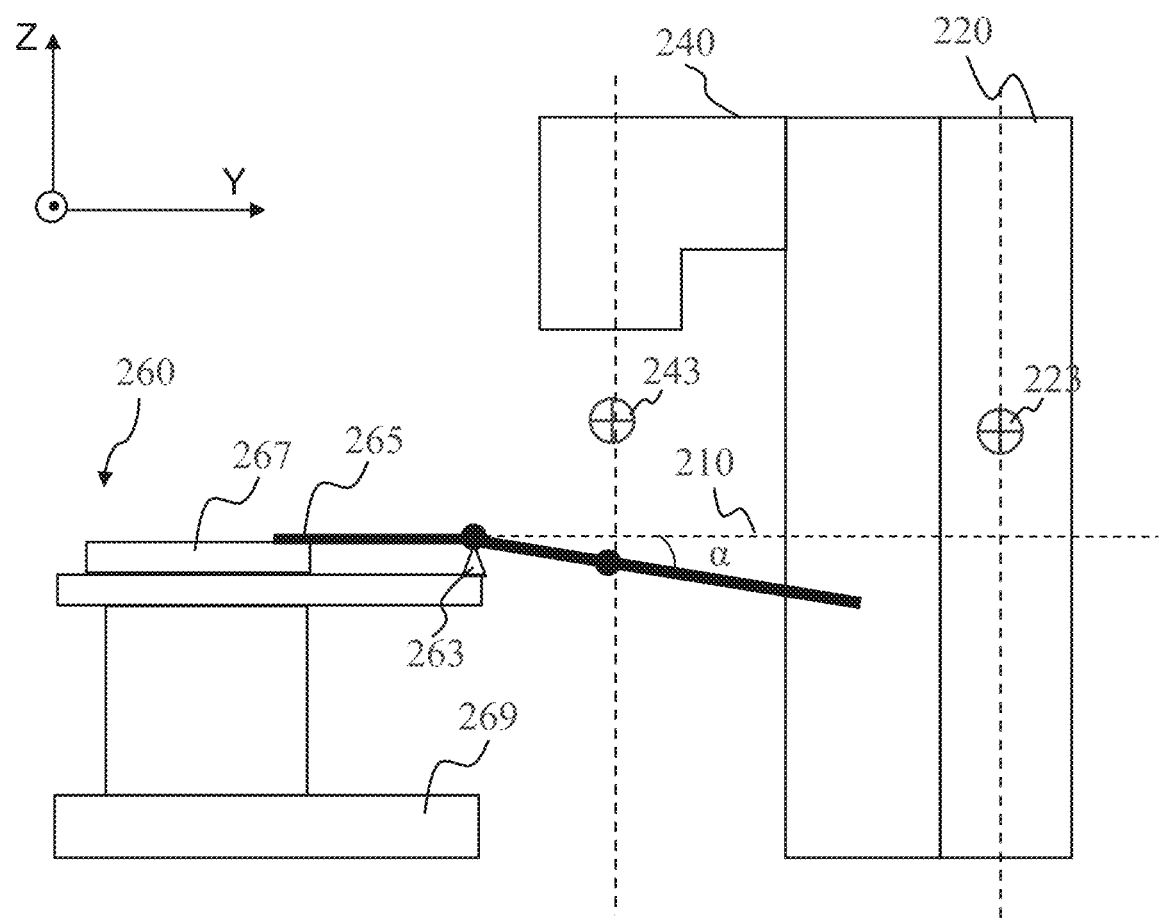
FIG. 2 illustrates a side view of an exemplary IGRT apparatus and associated components according to some embodiments of the present disclosure.

FIG. 2 illustrates a side view of an exemplary IGRT apparatus 200 and associated components according to some embodiments of the present disclosure. The IGRT apparatus 200 may be an exemplary medical apparatus 110 as shown in FIG. 1. The IGRT apparatus 200 may include an imaging device 220, a RT device 240, and a couch 260.

The imaging device 220 may acquire imaging data relating to at least one part of a subject and/or the couch 260 via scanning the at least one part of the subject. The imaging device 220 may include a CT scanner, a PET scanner, a SPECT scanner, an MRI scanner, or the like, or a combination thereof. In some embodiments, the imaging device 220 may have an isocenter 223. As used herein, the isocenter 223 of the imaging device 220 may refer to a point through which central rays of a radiation source of the imaging device 220 passes during a medical process.

The RT device 240 may be used for treatment, for example, performing a radio therapy on the at least one part of the subject determined based on the CT image. The RT device 240 may include a cyclotron, an induction accelerator, a linear accelerator (LINAC), etc. In some embodiments, the imaging device 220 and the RT device 240 may be set back to back or adjacent to each other as illustrated in FIG. 2. The imaging device 220 and the RT device 240 may have a same rotation axis. Specifically, the imaging device 220 may be coupled with the RT device 240. In some embodiments, the imaging device 220 and the RT device 240 may be set separately from each other. The RT device 240 may have an isocenter 243. As used herein, the isocenter 243 of the RT device 240 may refer to a point through which central rays of a radiation source of the RT device 240 passes during a medical process. The isocenter 223 of the imaging device 220 and the isocenter 243 of the RT device 240 may lie on a same horizontal longitudinal line.

The couch 260 may be configured to support and/or transfer the at least one part of the subject. The couch 260 may include a support roller 263, a table top 265, a table top carrier 267, a table base 269, or the like, or any combination thereof. The support roller 263 may support the table top carrier 267. The table top carrier 267 may support the table top 265. The table top 265 may extend along the longitudinal direction of the couch.

The couch 260 may move in any direction. For example, a longitudinal direction (i.e., along a long axis of table top 265 in the plane of the table top 265), a lateral direction (i.e., along a short axis of the table top 265 in the plane of the table top 265), a direction (also referred to as a vertical direction) perpendicular to the longitudinal direction and lateral direction, or a direction oblique to the longitudinal direction and/or the lateral direction. The movement of the couch 260 may be driven manually or by, for example, a motor. In some embodiments, the longitudinal direction may be described as Y direction. The vertical direction may be described as the Z direction. The Y direction and the Z direction may be within the plane containing a radiotherapy source of the RT device 240 and the rotation centers of the RT device 240 and the imaging device 220.

In some embodiments, the imaging device 220 and the RT device 240 may share the couch 260. An object supported on the couch 260 may go through both an imaging scan and a radiation therapy during which the object does not need to change from one couch to a different couch. For example, the couch 260 may be used to support an object at an RT position for a radiation therapy. As another example, the couch 260 may be used to transfer an object from an RT position to an imaging position and/or support the object at the imaging position for imaging. As used herein, an RT position may refer to a position that is within a work area of the RT device 240. A CT position may refer to a position that is within a work area of the imaging device 220.

The couch 260 (e.g., the table top 265) may include a plurality of positions. While the couch 260 extends from an RT position under the radiation source of the RT device 240 and then further into an imaging position under the imaging device 220, the couch 260 may deform. The deformation of a specific position of the table top 265 extending beyond the support roller 263 may change as the table top 265 extends or retracts. The deformation element at the specific position of the table top 265 may increase along with the increase of the amount of extension. In some embodiments, the deformation of a position of the table top 265 located at the support roller 263 may be neglected. The position of the table top 265 located at the support roller 263 may be designated as a reference position of the couch 260. For each of the plurality of positions of the table top 265, the deformation of the couch 260 may be different when the couch 260 is located at a specific imaging position or RT position.

In some embodiments, the deformation of a couch corresponding to each of the plurality of positions of the table top 265 may be described in terms of a rotation angle (e.g., a as shown in FIG. 2) and a deformation element (e.g., the amount of displacement of a couch in the vertical direction, etc.) associated with the each of the plurality of positions of the table top 265. The rotation angle may be an angle between the dashed line 210 and the deformed section of the table top 265 that extends beyond the supporting structure (e.g., the table top carrier 267) of the table top 265. In some embodiments, the deformation of a couch may be described in terms of a displacement field with respect to a reference conformation of the couch (e.g., a conformation of the couch without deformation). The displacement field may include a plurality of displacement components. Each of the plurality of displacement components may correspond to one of the plurality of positions of the table top 265 with respect to the reference conformation at the one of the plurality of positions. More descriptions of the displacement field and/or the rotation angles may be found elsewhere in the present disclosure. See for example, FIGS. 6-10 and the descriptions thereof.

FIG. 3 is a schematic diagram illustrating exemplary hardware and/or software components of an exemplary computing device 300 on which the processing device 120 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process imaging data obtained from the medical apparatus 110, the storage 130, terminal(s) 140, and/or any other component of the diagnostic and treatment system 100. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 300. However, it should be noted that the computing device 300 in the present disclosure may also include multiple processors, thus operations and/or method steps that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the medical apparatus 110, the storage 130, the terminal(s) 140, and/or any other component of the diagnostic and treatment system 100. In some embodiments, the storage 320 may include a mass storage, a removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 120 for determining a target flip angle schedule.

The I/O 330 may input and/or output signals, data, information, etc. In some embodiments, the I/O 330 may enable a user interaction with the processing device 120. In some embodiments, the I/O 330 may include an input device and an output device. Examples of the input device may include a keyboard, a mouse, a touch screen, a microphone, or the like, or any combination thereof. Examples of the output device may include a display device, a loudspeaker, a printer, a projector, or the like, or any combination thereof. Examples of the display device may include a liquid crystal display (LCD), a light-emitting diode (LED)-based display, a flat panel display, a curved screen, a television device, a cathode ray tube (CRT), a touch screen, or the like, or any combination thereof.

The communication port 340 may be connected to a network (e.g., the network 150) to facilitate data communications. The communication port 340 may establish connections between the processing device 120 and the medical apparatus 110, the storage 130, and/or the terminal(s) 140. The connection may be a wired connection, a wireless connection, any other communication connection that can enable data transmission and/or reception, and/or a combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or any combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
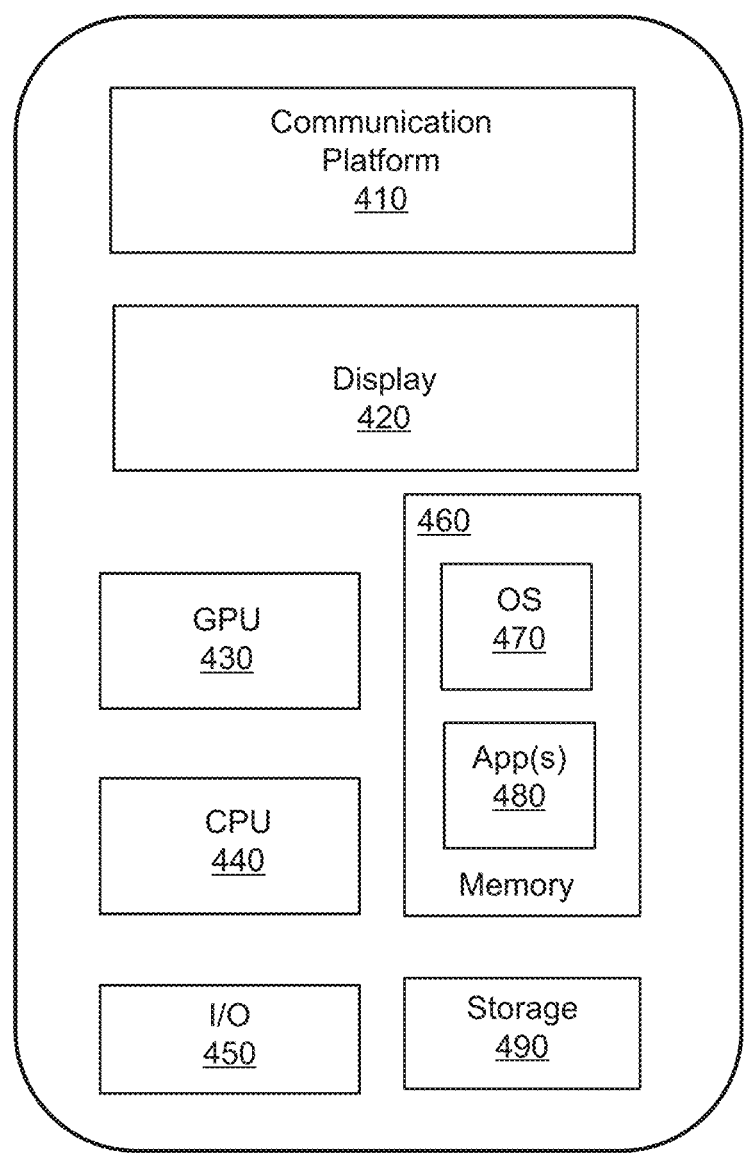
FIG. 4 is a schematic diagram illustrating exemplary hardware and/or software components of an exemplary mobile device on which the terminal may be implemented according to some embodiments of the present disclosure.

FIG. 4 is a schematic diagram illustrating exemplary hardware and/or software components of an exemplary mobile device 400 on which the terminal(s) 140 may be implemented according to some embodiments of the present disclosure. As illustrated in FIG. 4, the mobile device 400 may include a communication platform 410, a display 420, a graphic processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 120. User interactions with the information stream may be achieved via the I/O 450 and provided to the processing device 120 and/or other components of the diagnostic and treatment system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
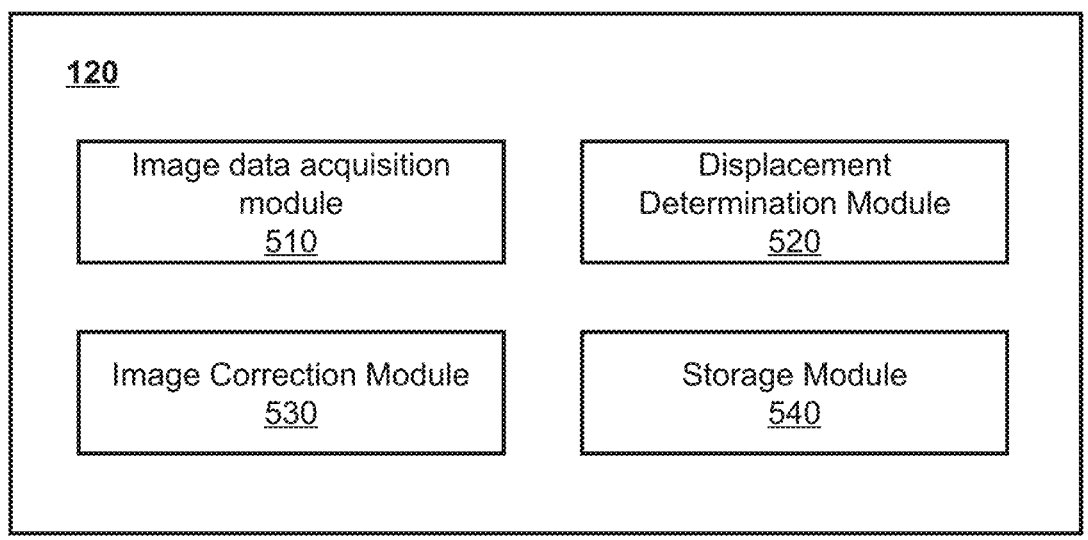
FIG. 5 is a block diagram illustrating an exemplary processing device according to some embodiments of the present disclosure.

FIG. 5 is a block diagram illustrating an exemplary processing device 120 according to some embodiments of the present disclosure. The processing device 120 may be implemented on the computing device 300 (e.g., the processor 310) illustrated in FIG. 3 or the mobile device 400 as illustrated in FIG. 4. The processing device 120 may include an image data acquisition module 510, a displacement determination module 520, an image correction module 530, and a storage module 540.

The image data acquisition module 510 may obtain imaging data relating to a subject and/or a couch supporting the subject. The imaging data relating to a subject and/or a couch supporting the subject may be presented as a stack of image slices affording sagittal views, a stack of image slices affording coronal views, a stack of image slices affording axial views, spatial basis function representations, or a combination thereof. In some embodiments, the imaging data may be obtained from the medical apparatus 110, the storage 130, the terminal(s) 140, the storage module 540, or any other external storage. For example, the imaging data may be obtained from the medical apparatus 110 generated by the imaging device 112 scanning the subject.

The displacement determination module 520 may determine a displacement field associated with imaging data. In some embodiments, the displacement field associated with imaging data may include a plurality of displacement components. The displacement field associated with images in a view corresponding to the imaging data may be converted to a displacement field associated with images corresponding to the same imaging data in a different view. For instance, the displacement field associated with images in the sagittal view corresponding to the imaging data may be converted to a displacement field associated with images corresponding to the same imaging data in the axial view and/or in the coronal view. The imaging data adjusted based on a displacement field associated with images in a view (e.g., in an axial view) may be used to provide adjusted images in another view (e.g., in a coronal view). For instance, the imaging data adjusted based on a displacement field associated with images in the sagittal view may be used to provide adjusted images in the axial view and/or the coronal view. For illustration purposes, the displacement field associated with images in the sagittal view is described below. It is understood it is not intended to limit the scope of the present disclosure. A displacement component of the plurality of displacement components may correspond to a position of the plurality of positions of a couch. In some embodiments, the displacement determination module 520 may determine a displacement component based on a first conformation of the couch reflected in the imaging data and a reference conformation. In some embodiments, a displacement component corresponding to a position of the couch may include a rotation angle associated with the position. The displacement determination module 520 may determine the rotation angle associated with the position.

The image correction module 530 may adjust the imaging data based on the displacement field associated with the imaging data. In some embodiments, the image correction module 530 may move the pixels or voxels in the imaging data based on the displacement field. In some embodiments, the image correction module 530 may move a plurality of spatial basis function representations associated with the imaging data based on the displacement field. In some embodiments, the image correction module 530 may obtain an image based on the adjusted imaging data.

The storage module 540 may store information. The information may include programs, software, algorithms, data, text, number, images and some other information. For example, the information may include imaging data, a displacement field associated with the imaging data, etc. The displacement field may include a plurality of displacement components associated with the imaging data.

It should be noted that the above description of the processing device 120 is provided for the purpose of illustration, and is not intended to limit the scope of the present disclosure. For persons having ordinary skills in the art, multiple variations and modifications may be made under the teaching of the present disclosure. However, those variations and modifications do not depart from the scope of the present disclosure.

FIG. 6 is a flowchart illustrating an exemplary process for correcting an image slice according to some embodiments of the present disclosure. In some embodiments, one or more operations of process 600 illustrated in FIG. 6 may be implemented in the diagnostic and treatment system 100 illustrated in FIG. 1. For example, process 600 illustrated in FIG. 6 may be stored in the storage 130 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4).

In 602, a first set of imaging data may be obtained. The first set of imaging data may afford a sagittal view relating to a subject and a couch supporting the subject. Operation 602 may be performed by the image data acquisition module 510. The couch may have a plurality of first positions reflected in the first set of imaging data as a first conformation. For brevity, a position of a couch as used herein may refer to a physical portion of the couch, or the corresponding portion as reflect in the imaging data or in an image (or image slice). For brevity, a conformation of a couch may refer to a contour or outline of the couch physically, or the corresponding contour or outline as reflect in the imaging data or in an image (or image slice). For example, the first conformation of the couch may refer to the shape or outline of the couch supporting the subject reflected in the first set of imaging data. The first conformation of the couch may relate to the configurations of the couch at various positions. The first conformation of the couch may depend on factors including, e.g., its supporting structure, the material of the couch, the loading placed on the couch, or the like, or a combination thereof. In some embodiments, the first set of imaging data may be obtained from the medical apparatus 110, the storage 130, the terminal(s) 140, the storage module 540, or any other external storage. For example, the first set of imaging data may be obtained from the medical apparatus 110 generated by the imaging device 112 scanning the subject. The imaging device 112 may include a CT device, a CBCT device, a PET device, a volume CT device, an MRI device, a SPECT device, or the like, or a combination thereof.

In some embodiments, the first set of imaging data may be presented in the form of spatial basis function representations relating to the subject and the couch. Each of the plurality of first positions or the first conformation at the each of the plurality of first positions reflected in the first set of imaging data may correspond to one of the plurality of spatial basis function representations. The spatial basis function representations relating to the subject and the couch may refer to information of a first image (or referred to as a first image slice) relating to the subject and the couch in a spatial domain represented based on multiple spatial basis functions in a transform domain. The spatial basis function representations (i.e., the first set of imaging data) relating to the subject and the couch may be obtained by performing a positive transformation on the first image relating to the subject and the couch based on a plurality of spatial basis functions, then the first image in the spatial domain may be transformed into the first set of imaging data in the transform domain. As used herein, the spatial basis functions may be also referred to as basis vectors, dictionary elements, elementary functions, etc. The spatial basis function representations (i.e., the first set of imaging data) in the transform domain may be transformed into the first image in the spatial domain by performing a negative transformation on the spatial basis function representations (i.e., the first set of imaging data) based on the plurality of spatial basis functions. Exemplary transformations may include a Fourier transform (FT), a Wavelet transform (WT), independent component analysis (ICA), sparse coding (SC), a Gabor transform, or the like, or a combination thereof. Exemplary transformations may include a Fourier transform (FT), a Wavelet transform (WT), an independent component analysis (ICA), sparse coding (SC), a Gabor transform, or the like, or a combination thereof.

Figure 9:
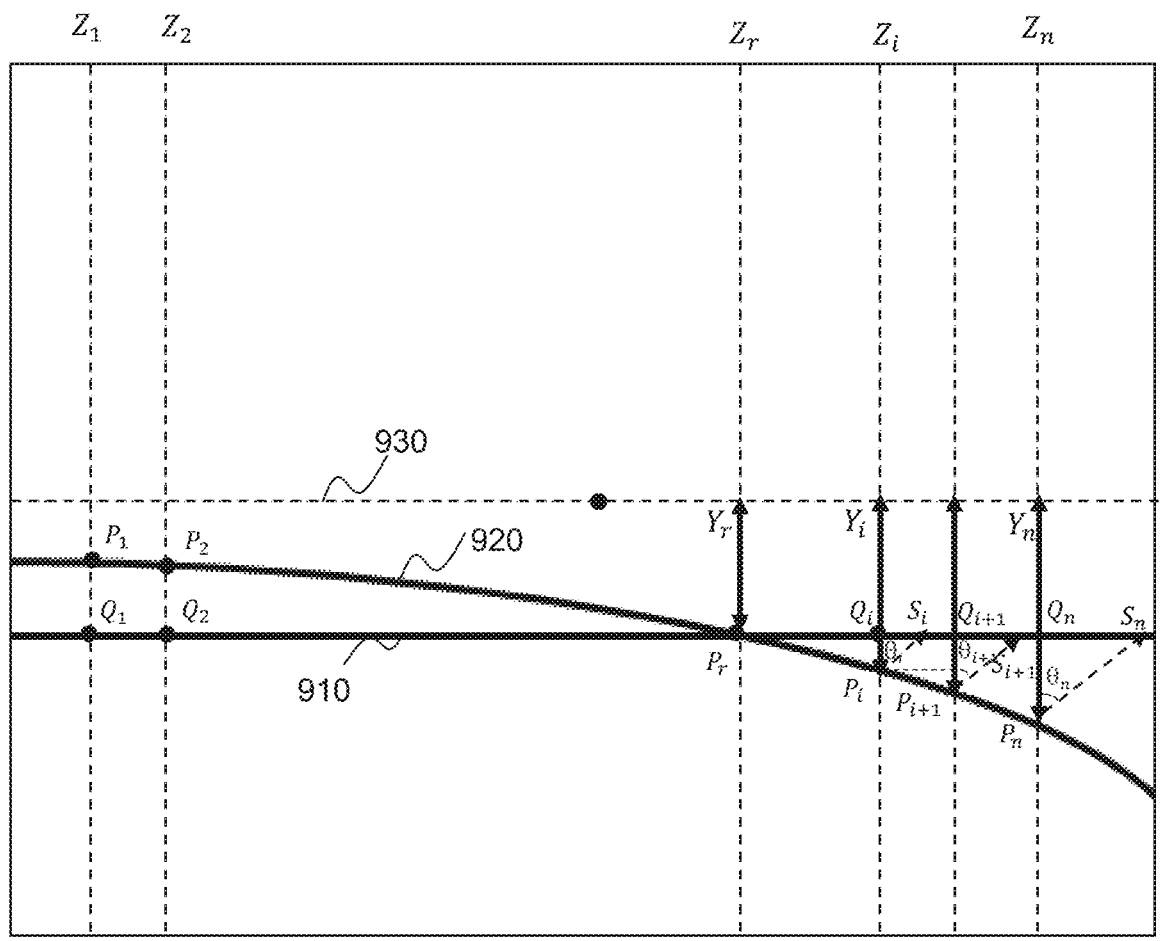
FIG. 9 is a schematic diagram illustrating an example for determining a displacement component according to some embodiments of the present disclosure.

In 604, a displacement field associated with the first set of imaging data with respect to a reference conformation may be determined based on the first conformation and a reference conformation. Operation 604 may be performed by the displacement determination module 520. As used herein, the reference conformation may be also referred to as a model conformation of the couch. For example, the first conformation may be reflected in the first image affording a sagittal view as a first line (e.g., line 920 as shown in FIG. 9). The reference conformation may be reflected in the first image affording the sagittal view as a second line (e.g., line 910 as shown in FIG. 9). In some embodiments, the second line may be a straight horizontal line. The second line (e.g., line 910 as shown in FIG. 9) may intersect with the first line (e.g., line 920 as shown in FIG. 9) at a reference point (e.g., point $P_r$ as shown in FIG. 9) corresponding to the reference position of the couch. The reference conformation and the first conformation of the couch reflected in the first set of imaging data may be the same at the reference position. The deformation or configuration of the couch with the reference conformation may be the same as the deformation or configuration of the couch with the first conformation at the reference position. In some embodiments, the reference conformation of the couch may be determined by determining a reference position of the couch reflected in the first set of imaging data. The reference conformation of the couch reflected in the first set of imaging data (i.e., the second line) may be determined by determining a straight horizontal line through the reference point on the first line.

In some embodiments, the reference conformation may include a conformation of the couch without deformation. The first set of imaging data may be adjusted based on the displacement field corresponding to the reference conformation so that the adjusted first set of imaging data may present the subject or a portion thereof supported on a couch without deformation.

In some embodiments, the reference conformation of the couch may include a conformation of the couch with deformation that is different from deformation of the couch corresponding to the first conformation. In some embodiments, the reference conformation of a couch may be obtained from a second set of imaging data affording a sagittal view relating to the couch. The second set of imaging data may be acquired when the couch supports the subject or not. In some embodiments, the couch reflected in the second set of imaging data may be the same as the couch reflected in the first set of imaging data. For instance, the first set of imaging data and the second set of imaging data may be acquired by scanning the subject using a same imaging device including a couch for supporting the subject (e.g., a same CT scanner in a same IGRT device, a same imaging device 112 of the medical apparatus 110). In some embodiments, the couch reflected in the second set of imaging data may be different from the couch reflected in the first set of imaging data. For instance, the first set of imaging data and the second set of imaging data may be acquired by scanning the subject using different imaging devices having different couches for supporting the subject, e.g., a CT scanner in an IGRT device and a different CT scanner. The first set of imaging data may be adjusted based on the displacement field corresponding to the reference conformation so that the adjusted first set of imaging data relating to the subject or a portion thereof may be registered and/or compared with the second set of imaging data relating to the same subject or a portion thereof.

As used herein, the displacement field associated with the first set of imaging data may reflect changes of positions of the couch reflected in the first set of imaging data (e.g., the first conformation) with respect to the reference conformation. The displacement field associated with the first set of imaging data may also reflect changes of positions of the subject corresponding to and represented by the changes of the first conformation with respect to the reference conformation.

The displacement field may include a plurality of displacement components. A displacement component may correspond to a position or a spatial basis representation function of the couch. A displacement component may reflect a local displacement at a position or correspond to a spatial basis representation function of the couch. The displacement component associated with the first position may include a distance from the first position to a corrected first position of the first couch with respect to the reference conformation and a direction from the first position to the corrected first position of the first couch with respect to the reference conformation reflected in the first set of imaging data. Two displacement components corresponding to two different first positions or two different spatial basis function representations respectively may be different. A displacement component associated with the reference position may equal 0. In other words, the distance from the reference position to a corrected reference position of the first couch with respect to the reference conformation may equal 0. The first conformation may coincide with the reference conformation at the reference position. In some embodiments, a distance between a first position and the reference position reflected in the first set of imaging data and a distance between an adjacent first positon and the reference position reflected in the reflected in the first set of imaging data may be different. In some embodiments, these distances may change as a function of the first positions nonlinearly. See, e.g., FIG. 9. In some embodiments, a distance from the first position to a corrected first position of the first couch with respect to the reference conformation may relate to a distance between the reference position of the couch and the first position of the couch. In some embodiments, the distance between the reference position of the couch and the first position of the couch may be assessed in terms of or approximated by a length of a portion of the couch between the reference position and the first position of the couch. Further, the reference position may correspond to a spatial basis function representation. The first position may correspond to a spatial basis function representation. The displacement component associated with the first position may relate to a distance (e.g., the length of a portion of the couch between the reference position and the first position of the couch) between the spatial basis function representation corresponding to the first position and the reference basis function representation corresponding to the reference position.

In some embodiments, a direction from the first position to the corrected first position of the first couch with respect to the reference conformation may be defined by a rotation angle associated with the first positon. The displacement field associated with the first of imaging data may include a plurality of rotation angles as described elsewhere in the present disclosure (e.g., FIG. 2, and the descriptions thereof). A rotation angle may correspond to a first position of the couch. In some embodiments, a rotation angle may relate to a spatial basis function representation associated with the first set of imaging data. Two rotation angles corresponding to two different first positions or two different spatial basis function representations respectively may be different. In some embodiments, the rotation angle associated with a first position of the couch may relate to a distance between the reference position of the couch and the first position of the couch as reflected in the first set of imaging data. In some embodiments, the distance between the reference position of the couch and the first position of the couch may be assessed in terms of or approximated by a length of a portion of the couch between the reference position and the first position of the couch. In some embodiments, the longer the distance (e.g., the length of the portion of the couch) between the reference position and the first position is, the greater the rotation angle associated with the first position of the couch may be. The rotation angle associated with the first position may relate to a distance between the spatial basis function representation corresponding to the first position and the reference basis function representation corresponding to the reference position. In some embodiments, the greater the distance between the spatial basis function representation and the reference basis function representation is, the greater the rotation angle associated with the first position may be.

In some embodiments, the rotation angle associated with a first position may be determined based on a distance (e.g., a length of a portion of the couch) between the reference position and the first position reflected in the first set of imaging data, an offset in a vertical direction of the first conformation at the first position from the reference conformation, and/or a distance in a horizontal direction between a reference position and the first position. As used herein, the offset in a vertical direction may also be referred to as a deformation element in a vertical direction of the first conformation at the first positon from the reference conformation. More descriptions for determining a rotation angle associated with a position of a couch may be found elsewhere in the present disclosure. See for example, FIG. 8 and FIG. 9 and the descriptions thereof.

In 606, the first set of imaging data may be adjusted based on the displacement field associated with the first set of imaging data with respect to the reference conformation. Operation 606 may be performed by the image correction module 530. In some embodiments, the first set of imaging data may be adjusted by moving the plurality of spatial basis function representations based on the displacement field. For example, a spatial basis function representation may correspond to a rotation angle. A spatial basis function representation may be adjusted based on a rotation angle corresponding to the spatial basis function representation. In some embodiments, the adjustment may be performed, based on the displacement field, on the pixel or voxel basis with respect to the first set of imaging data. In some embodiments, the first set of imaging data affording to the sagittal view may correspond to second set of imaging data affording to an axial view. The first set of imaging data may be adjusted by adjusting the second set of imaging data affording to the axial view based on the displacement field. Further, the adjustment may be performed on pixels or voxels with respect to the second set of imaging data based on the displacement field. The first set of imaging data may be determined based on the adjusted second set of imaging data. In some embodiments, imaging data in the second set of imaging data corresponding to the reference position of the couch does not need to be adjusted.

In 608, an image of the subject with respect to the reference conformation may be obtained based on the adjusted first set of imaging data. Operation 608 may be performed by the image correction module 530. In some embodiments, the image of the subject with respect to the reference conformation may be obtained by performing a negative transformation on the adjusted first set of imaging data based on the plurality of spatial basis functions as described in 602. Further, the adjusted spatial basis function representations may be transformed into one or more images of the subject. The imaging data adjusted based on a displacement field associated with images in a view (e.g., in a sagittal view) may be used to provide adjusted images in another view (e.g., in a coronal view). The adjusted first set of imaging data may be used to generate an adjusted 3D image. The adjusted first set of imaging data may be used to generate one or more adjusted 2D image slices in one or more planes, e.g., one or more sagittal planes, one or more coronal planes, one or more axial planes, one or more same or different oblique planes. For instance, the adjusted first set of imaging data may be used to generate a series of 2D image slices in different axial planes, or a series of 2D image slices in different sagittal planes, or a series of 2D image slices in different coronal planes, or one or more 2D image slices in parallel or nonparallel oblique planes.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, process 600 may include obtaining the first image affording a sagittal view corresponding to the first set of imaging data and transforming the first image into the first set of imaging data based on a plurality of spatial basis functions. As another example, process 600 may further include obtaining a second set of imaging data affording a sagittal view relating to the subject and the couch and determining the reference conformation based on the second set of imaging data. The couch may include a plurality of second positions reflected in the second set of imaging data as the reference conformation.

FIG. 7 is a flowchart illustrating an exemplary process for correcting an image slice according to some embodiments of the present disclosure. In some embodiments, one or more operations of process 700 illustrated in FIG. 7 may be implemented in the diagnostic and treatment system 100 illustrated in FIG. 1. For example, process 700 illustrated in FIG. 7 may be stored in the storage 130 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4). With respect to 604, the reference conformation may correspond to the second conformation of the second couch, the first conformation may correspond to the first conformation of the first couch referred to in the description of FIG. 7, and the second stack of image slices are omitted.

In 702, a first image slice may be obtained. The first image slice may afford a sagittal view relating to an ROI of a subject and a first couch supporting the subject. The first couch may include a plurality of first positions reflected in the first image slice as a first conformation. Operation 702 may be performed by the image data acquisition module 510. In some embodiments, the first image slice may be obtained based on a first set of imaging data. The first set of imaging data may be obtained from the storage 130, the terminal(s) 140, the storage module 540, or any other external storage. In some embodiments, the first set of imaging data may be acquired by scanning the subject supported on the second couch using a first device (e.g., the medical apparatus 110) including an imaging device. Exemplary imaging devices may include a CT device, a CBCT device, a PET device, a volume CT device, an MRI device, a SPECT device, etc. The first device may further include an interventional medical device, for example, a radiation therapy treatment (RT) device, an ultrasound treatment device, a thermal treatment device, a surgical intervention device, or the like, or a combination thereof.

In some embodiments, the first set of imaging data may be presented as a first stack of image slices affording sagittal views, a first stack of image slices affording coronal views, a first stack of image slices affording axial views, spatial basis function representations, or a combination thereof. The first image slice may correspond to the first stack of image slices affording axial views relating to the ROI of the subject and the first couch. An image slice of the first stack affording an axial view may correspond to a first position of the first couch.

In some embodiments, the first conformation may be reflected in the first image slice affording the sagittal view as a first line. The first image slice may include a portion corresponding to the isocenter of the first device acquiring the first set of imaging data. For brevity, as used herein, an isocenter of a device (e.g., the imaging device 112) may refer to the isocenter of the physical device, or a portion of an image slice or imaging data that corresponds to the isocenter of the physical device.

In some embodiments, the first image slice affording the sagittal view may include a guiding image relating to the ROI of the subject. As used herein, a guiding image may be used to guide the implementation of the treatment plan of the subject. For example, the guiding image relating to the ROI of the subject may be used to position the ROI. The positioned ROI may receive radiation according to the treatment plan. The guiding image may be taken during or before the radiation therapy (e.g., on the day of treatment, or hours before the treatment, or minutes before the treatment, or seconds before the treatment, or during the treatment).

In 704, a second image slice may be obtained. The second image slice may afford a sagittal view relating to the ROI of the subject and a second couch supporting the subject. The second couch may include a plurality of second positions reflected in the second image slice as a second conformation. Operation 704 may be performed by the image data acquisition module 510. A second position of the second couch may correspond to a first position of the first couch. As used herein, a second position may be considered to correspond to a first position if the first position and the second position are located away from a reference position by a same distance (e.g., $P_i$ and $Q_i$ as illustrated in FIG. 9). In some embodiments, the second conformation may be reflected in the second image slice as a second line.

In some embodiments, the second image slice may be obtained based on a second set of imaging data. In some embodiments, the second set of imaging data may be obtained from the storage 130, the terminal(s) 140, the storage module 540, or any other external storage. In some embodiments, the second set of imaging data may be acquired by scanning the subject supported on the second couch using a second device. The second device may include a CT device, a CBCT device, a PET device, a volume CT device, an MRI device, a SPECT device, or the like, or a combination thereof.

In some embodiments, the second set of imaging data may be presented as a second stack of image slices affording sagittal views, a second stack of image slices affording coronal views, a second stack of image slices affording axial views, spatial basis function representations, or a combination thereof. The second image slice may correspond to the second stack of image slices affording axial views relating to the ROI of the subject and the second couch. An image slice of the second stack affording an axial view may correspond to a second position of the second couch. The second image slice affording a sagittal view may include a portion corresponding to the isocenter of the second device acquiring the second set of imaging data.

In some embodiments, the second image slice may include a planning image relating to the ROI of the subject. As used herein, a planning image may be used to design a treatment plan of the subject. For example, the planning image may be taken before the subject receives a radiation therapy (e.g., days or weeks before). The planning image may be used to identify a focus, a treatment target (e.g., the ROI of the subject), an organ at risk, and the external contour of the subject, and the treatment plan may be designed for the subject based on the planning image.

In some embodiments, the first couch and the second couch may be the same couch. For instance, the first set of imaging data and the second set of imaging data may be acquired by scanning the subject using a same imaging device including a couch for supporting the subject (e.g., a same CT scanner in a same IGRT device, a same imaging device 112 of the same medical apparatus 110). In some embodiments, the first couch and the second couch may be two different couches. For instance, the first set of imaging data and the second set of imaging data may be acquired by scanning the subject using different imaging devices having different couches for supporting the subject, e.g., a CT scanner in an IGRT device and a different CT scanner.

In 706, a displacement field associated with the first image slice may be determined based on the first conformation and the second conformation. Operation 706 may be performed by the displacement determination module 520. The displacement field may include a plurality of displacement components. A displacement component may be associated with a first position. As used herein, a displacement component may reflect a change of a position of the first couch reflected in the first image slice (e.g., the first conformation) with respect to the second conformation. At least two displacement components of the plurality of displacement components may be different. The displacement components may be local, depending on their corresponding first positions of the first couch. The displacement component associated with the first position may include a distance from the first position to a corrected first position of the first couch with respect to the second conformation and a direction from the first position to the corrected first position of the first couch with respect to the second conformation reflected in the first image slice. In some embodiments, a distance between a first position and the reference position reflected in the first image slice and a distance between an adjacent first positon and the reference position reflected in the reflected in the first image slice may be different. In some embodiments, these distances may change as a function of the first positions nonlinearly. See, e.g., FIG. 9. A displacement component associated with the reference position may equal 0. In other words, the distance between the reference position and a corrected reference position of the first couch with respect to the second conformation may equal 0. The first conformation may coincide with the second conformation at the reference position. A distance from the first position to the corrected first position of the first couch with respect to the second conformation may relate to the distance between a reference position and the first position reflected in the first image slice. In some embodiments, the distance between the reference position and the first position may be assessed in terms of or approximated by a length of a portion of the first portion between the reference position and the first position. In some embodiments, the longer the distance (e.g., the length of a portion of the first couch) between the reference position and the first position is, the greater the displacement component associated with the first position may be. As used herein, the reference position of the second couch or the reference position of the first couch may refer to a second position of the second couch or a corresponding first position of the first couch that the first conformation at the reference position of the first couch is the same as the second conformation of the second couch at the reference position. The reference position of the first couch or the reference position of the second couch may correspond to an intersection between the first conformation and the second conformation. The first conformation may coincide with the second conformation at the reference position. In some embodiments, the intersection between the first conformation and the second conformation may be determined by registering the first image slice and the second image slice. In some embodiments, the first image slice and the second image slice may be registered based on, e.g., a characteristic feature appearing in both image slices. Exemplary characteristic features may correspond to a common marker, a common feature, etc., of the subject and/or the first couch and the second couch. In some embodiments, the first image slice and the second image slice may be registered based on the isocenter of the first device acquiring the first image slice and the isocenter of the second device acquiring the second image slice. The isocenter of the first device acquiring the first image slice and the isocenter of the second device may be coincident in the third image slice.

In some embodiments, the displacement field associated with the first image slice may be determined by determining each of the plurality of displacement components corresponding to one first position of the first couch. A displacement component associated with a specific first position may be determined based on the first conformation reflected in the first image slice and the second conformation reflected in the second image slice. In some embodiments, the first conformation and the second conformation may be illustrated in one image slice. In some embodiments, the displacement component associated with the specific first position may be determined based on a distance (e.g., a length of a portion of the first couch) between the reference position and the specific first position reflected in the first image slice. The length of the portion of the first couch between the reference position and the specific first position may be determined based on a length of a section of the first conformation (i.e., the first line) between the reference position and the specific first position reflected in the first image slice.

In some embodiments, a direction from a specific first position to the corrected specific first position of the first couch with respect to the second conformation may be defined by a rotation angle associated with the specific first position. The rotation angle associated with the specific first position may relate to a distance (e.g., a length of a portion of the second couch) between the reference position to the specific first position reflected in the second image slice. In some embodiments, the longer the distance (e.g., the length of a portion of the first couch) between the reference position to a specific first position is, the greater the rotation angle associated with the specific first position may be. In some embodiments, the rotation angle associated with the specific first position may be determined based on the distance (e.g., the length of the portion of the first couch) between the reference position to the specific first position, an offset in a vertical direction of the first couch at the specific first position of the first conformation from the first conformation, and/or a distance in a horizontal direction between the reference position and the specific first position. More descriptions for determining a displacement component associated with a specific position may be found in FIG. 8 and/or FIG. 9.

In 708, the stack of third image slices may be adjusted based on the displacement field. Operation 708 may be performed by the image correction module 530. In some embodiments, the stack of third image slices may be adjusted by correcting each third image slice of the stack based on a displacement component associated with a first position corresponding to the each image slice of the first stack affording an axial view. Further, the each third image slice affording an axial view may be corrected by moving all pixels in the each image third slice of the stack based on the corresponding displacement component. In some embodiments, the stack of third image slices or the first image slice may correspond to a volume image (e.g., a three-dimension image) relating to the ROI and the first couch. The stack of third image slices may be adjusted by moving all voxels in the volume image based on the displacement field. In some embodiments, the stack of third image slices may correspond to imaging data relating to the ROI of the subject and the first couch. The imaging data may be presented as a plurality of spatial basis function representations as descried in connection with FIG. 6. The stack of third image slices may be adjusted by moving the plurality of spatial basis function representations based on the displacement field. Then, the adjusted stack of third image slices may be obtained based on the adjusted imaging data (i.e., the adjusted plurality of spatial basis function representations). The imaging data adjusted based on a displacement field associated with images in a view (e.g., in a sagittal view) may be used to provide adjusted images in another view (e.g., in a coronal view).

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 702 may be omitted. The first conformation may be designated as a reference conformation as described in FIG. 6. As another example, operations 702 and 704 may be performed simultaneously. In some embodiments, operation 708 may be omitted. For example, a third image slice in the stack of third image slices corresponding to the reference position of the first couch does not need to be adjusted based on a displacement component associated with the reference position.

Figure 8:
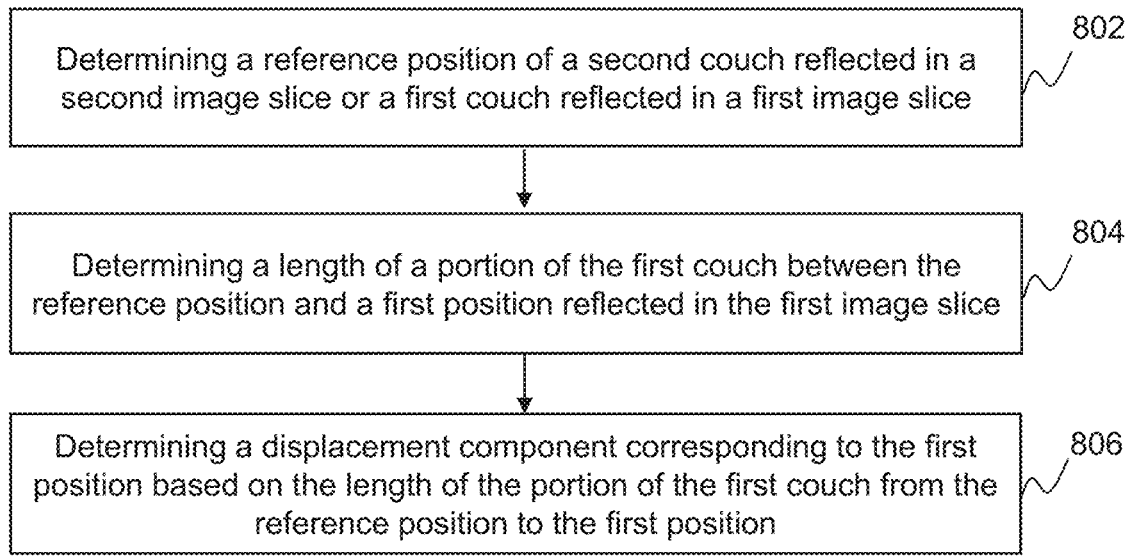
FIG. 8 is a flowchart illustrating an exemplary process for determining a displacement field associated with an image slice according to some embodiments of the present disclosure.

FIG. 8 is a flowchart illustrating an exemplary process for determining a displacement field associated with a second image slice according to some embodiments of the present disclosure. In some embodiments, one or more operations of process 800 illustrated in FIG. 8 may be implemented in the diagnostic and treatment system 100 illustrated in FIG. 1. For example, process 800 illustrated in FIG. 8 may be stored in the storage 130 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4). Operations 604 and 706 may be performed according to process 800 as illustrated in FIG. 8. With respect to 604, the reference conformation may correspond to the second conformation of the second couch, the first conformation may correspond to the first conformation of the first couch referred to in the description of FIG. 8, and the second image slice is omitted.

In 802, a reference position of a second couch reflected in a second image slice or a first couch reflected in a first image slice may be determined. Operation 802 may be performed by the displacement determination module 520. The first image slice relating to an ROI of a subject and the first couch supporting the subject may be obtained as described in connection with operation 702. The second image slice relating to the ROI of the subject and the second couch may be obtained as described in connection with operation 704. The first image slice and the second image slice may each afford a sagittal view. The first couch may include a plurality of first positions reflected in the first image slice as a first conformation. The second couch may include a plurality of second positions reflected in the second image slice as a second conformation. In some embodiments, the first image slice may correspond to a first stack of image slices relating to the ROI of the subject and the first couch affording axial views. The second image slice may correspond to a second stack of image slices relating to the ROI of the subject and the second couch affording the axial views. Each of the first positions may correspond to one image slice in the first stack. Each of the second positions may correspond to one image slice in the second stack. A second position of the second couch may correspond to a first position of the first couch.

The reference position of the second couch reflected in the second image slice and/or the first couch reflected in the first image slice may be determined based on the second conformation and the first conformation reflected in the second image slice and the first image slice, respectively. In some embodiments, the first conformation of the first couch may be segmented and/or identified from the first image slice as a first line (e.g., line 920 as shown in FIG. 9). A first position of the first couch may be reflected in the first image slice as a first point (e.g., point $P_1$ point $P_i$, point $P_{i+1}$, etc., as shown in FIG. 9). The second conformation of the second couch may be segmented and/or identified from the second image slice as a second line (e.g., line 910 as shown in FIG. 9). A second position of the second couch may be reflected in the second image slice as a second point (e.g., point $Q_1$, point $Q_i$, point $Q_{i+1}$, etc., as shown in FIG. 9). The reference positon of the second couch reflected in the second image slice or the first couch reflected in the first image slice may correspond to a reference point (e.g., point $P_r$ as shown in FIG. 9).

In some embodiments, the first image slice including the first line and the second image slice including the second line may be registered to form a third image slice (e.g., the image shown in FIG. 9) including the first line and the second line. For instance, the first positions on the first line corresponding to the first conformation may relate to the distances of the first couch from the floor at the first positions, and the second positions on the first line corresponding to the second conformation may relate to the distances of the second couch from the floor at the second positions; the second line may be reproduced in the first image slice based on the distances of the second couch from the floor at the second positions. As another example, the first image slice and the second image slice may be registered based on, e.g., a characteristic feature appearing in both image slices. Exemplary characteristic features may correspond to a common marker, a common feature, etc. As a further example, the first image slice and the second image slice may be registered based on an isocenter of a first device acquiring the first image slice and an isocenter of a second device acquiring the second image slice. The isocenter of the first device acquiring the first image slice and the isocenter of the second device may be coincident in the third image slice. An intersection point of the first line and the second line may be designated as the reference point (also referred to as the reference position of the second couch reflected in the second image slice or the first couch reflected in the first image slice).

In 804, a length of a portion of the first couch between the reference position and a first position reflected in the first image slice may be determined. Operation 804 may be performed by the displacement determination module 520. In some embodiments, the length (also referred to as a first length) of the portion of the first couch from the reference position to the first position reflected in the first image slice may be determined based on a length of a section of the first line (i.e., the first conformation reflected in the first image slice) from the reference point (e.g., point $P_r$ as shown in FIG. 9) to a first point (e.g., point $P_1$, point $P_2$, point $P_i$, point $P_{i+1}$, point $P_n$, etc., as shown in FIG. 9).

In some embodiments, a section of the first line from the reference point (e.g., point $P_r$ as shown in FIG. 9) to a first point (e.g., point $P_1$, point $P_2$, point $P_i$, point $P_{i+1}$, point $P_n$, etc., as shown in FIG. 9) may be considered as a straight line connecting the reference point and the first point. The length of the section of the first line from the reference point (e.g., point $P_r$ as shown in FIG. 9) to the first point (e.g., point $P_1$, point $P_2$, point $P_i$, point $P_{i+1}$, point $P_n$, etc., as shown in FIG. 9) may be equal to a distance between the reference point (e.g., point $P_r$ as shown in FIG. 9) and the first point (e.g., point $P_1$, point $P_2$, point $P_i$, point $P_{i+1}$, point $P_n$, etc., as shown in FIG. 9). The reference point may correspond to the reference position. A first point may correspond to a first position of the first couch. The distance between the reference point and the first point may be determined according to, e.g., a trigonometric relationship. For instance, the distance between the reference point and the first point may be determined as the hypotenuse of a right-angled triangle based on a first distance in a horizontal direction between the reference point and the first point and a second distance in a vertical direction between the reference point and the first point.

In some embodiments, the first distance in the horizontal direction between the reference point and the first point may be determined based on the interval between an image slice of the first stack corresponding to the reference position (e.g., position $Z_r$ as shown in FIG. 9) and an image slice of the first stack corresponding to the second position (e.g., position $Z_i$ as shown in FIG. 9). If the slice intervals between adjacent image slices are constant, the first distance in the horizontal direction may be determined based on the number of slices between the reference point and the second point and the slice intervals.

In some embodiments, the second distance (e.g., distance $Q_rP_i$ as shown in FIG. 9) in the vertical direction between the reference point and the second point may be also referred to as an offset in the vertical direction of the first conformation at the first position from the second conformation at the corresponding second position. The second distance (e.g., distance $Q_rP_i$ as shown in FIG. 9) in the vertical direction may be determined based on a distance (e.g., distance $Q_iP_i$ as shown in FIG. 9) between the first line and the second line at the first position, if the second line (line 910) is a horizontal straight line as illustrated in FIG. 9. For instance, as illustrated in FIG. 9, the second distance may be the difference between the distance $Y_iP_i$ in the vertical direction between the first point $P_i$ and a based line 930 and the distance $Y_iQ_i$ in the vertical direction between a corresponding point $Q_i$ on the second line to the line 930. As used herein, the base line may be a horizontal straight line passing the isocenter of a first device acquiring the first image slice.

In some embodiments, the first length of the portion of the first couch from the reference position to the first position reflected in the first image slice may be determined based on multiple section lengths of multiple portions of the first couch reflected in the first image slice. A section length may correspond to a pair of adjacent first positions of the first couch between the reference position and the first position reflected in the first image slice. A section length of a portion of the first couch between adjacent first positions may be determined based on a distance in a horizontal direction between the adjacent first positions (i.e., the slice interval) and an offset in the vertical direction of the first conformation at the adjacent first positions. The offset in the vertical direction of the first conformation at the adjacent first positions may be determined similarly to that described in connection with the determination of $Q_iP_i$, the description of which is not repeated. The first length of the portion of the first couch from the reference position to the first position reflected in the first image slice may be equal to a sum of the multiple section lengths.

In 806, a displacement component corresponding to the first position based on the first length of the portion of the first couch from the reference position to the first position may be determined. Operation 806 may be performed by the displacement determination module 520.

The displacement component associated with the first position may include a distance between the first position and a corrected first position of the first couch with respect to the second conformation and a direction from the first position to the corrected first position of the first couch with respect to the second conformation. In some embodiments, a distance between a first position and the reference position reflected in the first image slice and a distance between an adjacent first positon and the reference position reflected in the reflected in the first image slice may be different. In some embodiments, these distances may change as a function of the first positions nonlinearly. See, e.g., FIG. 9. In some embodiments, the displacement component corresponding to the reference position may equal 0. The distance between the reference position and a corrected reference position of the first couch with respect to the second conformation may be 0. The first conformation may coincide with the second conformation at the reference position. In some embodiments, the corrected first position of the first couch with respect to the second conformation may be determined in the first image slice based on the first length. As used herein, the corrected first position may refer to an ideal position of the first position in the first image slice after deformation correction of the first conformation with respect to the second conformation. The corrected first position of the first couch may be determined based on a second length of a portion of the first couch from the reference position to the corrected first position of the first couch with respect to the second conformation of the second couch. The second length may be determined based on the first length. In some embodiments, the second length may be equal to the first length.

In some embodiments, the second length may relate to an elastic extension of the portion of the first couch from the reference position to the first position. Further, the second length may be determined based on a difference between the elastic extension and the first length of the portion of the first couch between the reference position and the first position. In some embodiment, the elastic extension of the portion of the first couch between the reference position and the first position may be determined by simulating a stress distribution in the first couch with a load with the same weight of the subject using a numerical method (e.g., finite element method). The displacement component may then be determined based on the first position and the corrected first position reflected in the first image slice. For example, the first position may be reflected in the first image slice as the first point (e.g., point $P_i$, point $P_{i+1}$, point $P_n$, etc., as shown in FIG. 9). The corrected first position may be reflected in the first image slice as a corrected first point (e.g., point $S_i$, point $S_{i+1}$, point $S_n$, etc., as shown in FIG. 9). The displacement component may be determined based on a mapping from the first point (e.g., point $P_i$, point $P_{i+1}$, point $P_n$, etc., as shown in FIG. 9) to the corrected first point (e.g., point $S_i$, point $S_{i+1}$, point $S_n$, etc., as shown in FIG. 9). Further, the displacement component may be a vector (e.g., $P_iS_i$, $P_{i+1}S_{i+1}$, $P_{i+1}S_{i+1}$, etc., as shown in FIG. 9) from the first point to the corrected first point.

In some embodiments, the direction from the first position to the corrected first position of the first couch with respect to the second conformation may be defined by a rotation angle associated with the first positon. Two different first positions of the first couch may correspond to different rotation angles from the two first positions to two corrected first position of the first couch respectively with respect to the second conformation Then, the displacement component may be defined by a rotation angle and/or the offset in the vertical direction of the first conformation at the first positon from the second conformation. In some embodiments, the rotation angle associated with the reference positon may equal 0. In some embodiments, a rotation angle associated with the first position may be determined based on the first length, the first distance in the horizontal direction, and/or the second distance in the vertical direction. For example, the rotation angle associated with the first position may be determined based on the first length and the first distance in the horizontal direction using an inverse cosine function. As another example, the rotation angle associated with the first position may be determined based on the first length and the second distance in the vertical direction using an inverse sine function. As still an example, the rotation angle associated with the first position may be determined based on the first distance in the horizontal direction and the second distance in the vertical direction using an inverse tangent function or cotangent function. In some embodiments, the rotation angle associated with the first position may be an angle (e.g., angle $\theta_i$, angel $\theta_{i+1}$, angle $\theta_n$, etc., as shown in FIG. 9) between the displacement component (e.g., vector $P_iS_i$, vector $P_{i+1}S_{i+1}$, vector $P_nS_n$, etc., as shown in FIG. 9) and the second distance (e.g., distance $P_iQ_i$, distance $P_{i+1}Q_{i+1}$, distance $P_nQ_n$, etc., as shown in FIG. 9) in the vertical direction. The second distance in the vertical direction may be a component in the vertical direction of the displacement component. Then, the displacement component may be determined based on the rotation angle associated with the first position and the second distance in the vertical direction. More descriptions for determining the rotation angle may be found elsewhere in the present disclosure (e.g., FIG. 9, and the descriptions thereof).

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 804 may be divided into multiple operations, including determining a first distance in a horizontal direction from a reference position to a first position reflected in the first image slice, determining an offset in the vertical direction of the first couch at the first position with respect to the reference position, and determining the length of a portion of the second couch from the reference position to the first position reflected in the first image slice based on the first distance and the offset.

FIG. 9 is a schematic diagram illustrating an example for determining a displacement component according to some embodiments of the present disclosure. In some embodiments, the image shown in FIG. 9 may be obtained by registering a first image slice relating to a subject and a first couch and a second image slice relating to the subject and a second couch. The first image slice and the second image slice may afford a sagittal view. In some embodiments, the image shown in FIG. 9 may be obtained by adding a reference conformation to a first image slice relating to the subject and a first couch. In some embodiments, the line 910 may represent a second conformation of a second couch reflected in the image or the reference conformation. For illustration purposes, FIG. 9 is described with reference to the reference conformation. A line 920 represents a first conformation of a first couch reflected in the image. A line 930 represents a base line corresponding to a line passing the isocenter of the device acquiring the first image slice or second image slice. The first couch may include a plurality of first positions reflected in the image as multiple first points on the line 920 (e.g., point $P_1$, point $P_2$, point $P_i$, point $P_{i+1}$, point $P_n$, etc.). The reference conformation of the first couch may include a plurality of second positions reflected in the image as multiple second points on the line 910 (e.g., point $Q_1$, point $Q_2$, point $Q_i$, point $Q_{i+1}$, point $Q_n$, etc.). Point $P_r$ represents a reference position of the first couch. Point $P_r$ is an intersection of the line 910 and the line 920. A second position (e.g., point $Q_1$, point $Q_2$, point $Q_i$, point $Q_{i+1}$, point $Q_n$, etc.) and the corresponding first position (e.g., point $P_1$, point $P_2$, point $P_i$, point $P_{i+1}$, point $P_n$, etc.) correspond to the same image slice number affording an axial view corresponding to the first image slice.

A length of a portion of the first couch between a first position $P_i$ and the reference position $P_r$ reflected in the image may be determined based on a length (also referred to as length $L_{ir}$) of a section of the first line 920 between point $P_i$ corresponding to the first position $Z_i$ and reference point $P_r$. The length of the section of the line 920 between point $P_i$ and reference point $P_r$ may be determined according to Equation (1):

$$L_{ir} = \begin{cases} L_{i-1,r} + \sqrt{|Z_i - Z_{i-1}|^2 + |Y_i - Y_{i-1}|^2}, & r < i \le N \\ 0, & i = r \\ l_{i+1,r} + \sqrt{|Z_{i+1} - Z_i|^2 + |Y_{i+1} - Y_i|^2}, & 1 \le i < r \end{cases} \quad (1)$$

where Li, denotes the length of the section of the second line 1120 between point $P_i$ and reference point $P_r$, $|Z_i-Z_{i-1}|$ or $|Z_{i+1}-Z_i|$ denotes a distance in the horizontal direction between adjacent first positions reflected in the image slice, $Y_i$ denotes a distance between point $P_r$ and line 930, and $|Y_i-Y_{i-1}|$ or $|Y_{i+1}-Y_i|$ denotes an offset difference in the vertical direction of the first conformation between adjacent first positions reflected in the image slice. The offset difference in the vertical direction may also referred to as a deformation difference in the vertical direction of the first couch between adjacent first positions reflected in the image slice. Distances in the horizontal direction between adjacent first positions reflected in the image are equal to a slice interval $p_d$ between adjacent image slices affording axial views, such as $|Z_N-Z_{N-1}|=|Z_{N-1}-Z_{N-2}|= \ldots =|Z_2-Z_1|=p_d$.

In some embodiments, a length of a portion of the first couch between a first position $P_i$ and the reference position $P_r$ reflected in the image may be determined based on a distance between point $P_i$ and point $P_r$. The distance between point $P_i$ and point $P_r$ may be determined according to Equation (2) below:

$$P_r P_i = \sqrt{|Z_i - Z_r|^2 + |Y_i - Y_r|^2}, \quad (2)$$

where $P_r P_i$ denotes the distance between point $P_i$ and point $P_r$.

A displacement component $P_i S_i$ associated with the first position $P_i$ may be determined based on the length of the portion of the first couch between the first position $P_i$ and the reference position $P_r$ reflected in the image slice. A corrected first position of the first couch may be determined based on the length of the portion of the first couch between the first position $P_i$ and the reference position $P_r$ reflected in the image slice and the reference conformation. The corrected first position is reflected in the image slice as point $S_i$ on line 910. A length of a section of line 910 between point $P_r$ and point $S_i$ (also referred to as a distance between point $P_r$ and point $S_i$) corresponding to the corrected first position may be determined based on the length of the section of line 920 between point $P_r$ and point $P_i$ (also referred to as a distance between point $P_r$ and point $P_i$) corresponding to the first position. In some embodiments, a distance between a first point (e.g., the first point $P_i$) and the reference point $P_r$ reflected in the image slice and a distance between an adjacent first point (e.g., the first point $P_{i+1}$) and the reference point $P_r$ reflected in the image slice may be different. In some embodiments, these distances may change as a function of the first positions nonlinearly. See, e.g., FIG. 9. As used herein, an adjacent first point may correspond to an image slice in an axial view adjacent from the image slice including the first point in the axial view. The displacement component may be denoted as a vector $P_i S_i$. The displacement component associated with a first position (e.g., the first point $P_i$) may include a distance from the first point (e.g., the first point $P_i$) to a corrected first point (e.g., point $S_i$) and a direction from the first position (e.g., the first point $P_i$) to the corrected first position (e.g., point $S_i$).

In some embodiments, the direction of the displacement component associated with the first position $P_i$ may be defined by a rotation angle $\theta_i$. Rotation angle $\theta_i$ associated with the first position $P_i$ may be determined according to one of Equations (3)-(5) below:

$$\theta_i = \tan^{-1}\left(\frac{|Y_i - Y_r|}{|Z_i - Z_r|}\right), \quad (3)$$

$$\theta_i = \cos^{-1}\left(\frac{|Z_i - Z_r|}{L_{ir}}\right), \quad (4)$$

$$\theta_i = \sin^{-1}\left(\frac{|Y_i - Y_r|}{L_{ir}}\right). \quad (5)$$

A direction (e.g., rotation angle $\theta_i$) of a displacement component associated with a first position (e.g., the first position $P_i$) may be different from a direction (e.g., rotation angle $\theta_{i+1}$) of a displacement component associated with other first positions (e.g., the first position $P_{i+1}$, the first position $P_n$, etc.). The displacement component associated with the reference position (e.g., the reference point $P_r$) may equal 0. In other words, the distance between a corrected reference point (i.e., the reference point $P_r$) and the reference point (i.e., the reference point $P_r$) reflected in the image slice may equal 0. A rotation angle of the displacement component associated with the reference position (i.e., the reference point $P_r$) may equal 0.

FIG. 10 is a flowchart illustrating an exemplary process for correcting an image slice according to some embodiments of the present disclosure. In some embodiments, one or more operations of process 1000 illustrated in FIG. 10 may be implemented in the diagnostic and treatment system 100 illustrated in FIG. 1. For example, process 900 illustrated in FIG. 10 may be stored in the storage 130 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4). With respect to 604, the reference conformation may correspond to the second conformation of the second couch, the first conformation may correspond to the first conformation of the first couch referred to in the description of FIG. 10, and the second stack of image slices are omitted.

In 1002, a first stack of image slices may be obtained. The first stack of image slices may afford axial views relating to the ROI of the subject and a second couch supporting the subject. The first couch may have a plurality of first positions reflected in the first stack of image slices as a first conformation. Operation 1002 may be performed by the image data acquisition module 510. In some embodiments, the first stack of image slices may be obtained from the storage 130, the terminal(s) 140, the storage module 540, or any other external storage. In some embodiments, the first stack of image slices may be acquired by scanning the subject supported on the first couch using a first device. The first device may include a CT device, a CBCT device, a PET device, a volume CT device, an MRI device, a SPECT device, or the like, or a combination thereof.

The first stack of image slices affording axial views may correspond to a first image slice affording a sagittal view relating to the ROI of the subject and the first couch as described in connection with operation 702. An image slice of the first stack affording an axial view may correspond to a first position of the first couch.

In 1004, a second stack of image slices may be obtained. The second stack of image slice may afford the axial views relating to the ROI of the subject and a second couch supporting the subject. The second couch may have a plurality of second positions reflected in the second stack of image slices as a second conformation. Operation 1004 may be performed by the image data acquisition module 510. In some embodiments, the second stack of image slices may be obtained from the storage 130, the terminal(s) 140, the storage module 540, or any other external storage. In some embodiments, the second stack of image slices may be acquired by scanning the ROI of the subject supported on the second couch using a second device. In some embodiments, the second device may include a CT device, a CBCT device, a PET device, a volume CT device, an MRI device, a SPECT device, or the like, or a combination thereof.

The second stack of image slices affording axial views may correspond to a second image slice affording a sagittal view relating to the ROI of the subject and the second couch as described in connection with operation 704. An image slice of the second stack affording an axial view may correspond to a second position of the second couch. A second position of the plurality of second positions may correspond to a first position of the plurality of first positions. An image slice of the second stack may correspond to an image slice of the first stack.

In 1006, a displacement field associated with the first stack of image slices may be determined based on the first conformation and the second conformation. Operation 1006 may be performed by the displacement determination module 520. The displacement field may include a plurality of displacement components. A displacement component may be associated with a first position. An image slice of the first stack may correspond to a displacement component. In some embodiments, the displacement field associated with the first stack of image slices may be determined by determining each of the plurality of displacement components corresponding to one image slice of the first stack. A displacement component corresponding to an image slice of the first stack may be determined based on the first conformation at a first position reflected in the image slice of the first stack and the second conformation at a corresponding second position reflected in a corresponding image slice of the second stack.

The displacement component associated with a first position may include a distance between the first position and a corrected first position of the first couch with respect to the second conformation and a direction from the first position to the corrected first position of the first couch with respect to the second conformation reflected in the first stack of image slices. In some embodiments, a distance between a first position and the reference position reflected in the first stack of image slices and a distance between an adjacent first positon and the reference position reflected in the reflected in the first stack of image slices may be different. In some embodiments, these distances may change as a function of the first positions nonlinearly. See, e.g., FIG. 9. A displacement component associated with the reference position may equal 0. In other words, the distance between the reference position and a corrected reference position of the first couch with respect to the second conformation may equal 0. The first conformation may coincide with the second conformation at the reference position. In some embodiments, the distance between the first position and a corrected first position of the first couch with respect to the second conformation may be determined based on a distance (e.g., a length of a portion of the first couch) reflected in the first stack of image slices between a reference position and a specific first position corresponding to the image slice. The reference position of the first couch may be determined as descried elsewhere in the present disclosure (e.g., FIGS. 6-9, and the descriptions thereof). In some embodiments, the length of the portion of the first couch between the reference position and the specific first position may be determined based on a first distance in a horizontal direction and a second distance in a vertical direction between the reference position and the specific first position reflected in the first stack of image slices. The first distance in the horizontal direction may be determined based on an interval between an image slice of the first stack corresponding to the reference position and an image slice of the first stack corresponding to the specific first position. The second distance in the vertical direction may also referred to as an offset of the first conformation at the specific first position from the second conformation at a second position corresponding to the specific first position. The second distance in the vertical direction may be determined based on the first conformation reflected in the image slice of the first stack corresponding to the specific first position and the second conformation reflected in a corresponding image slice of the second stack.

In some embodiments, the direction from the first position to the corrected first position of the first couch with respect to the second conformation may be defined by a rotation angle associated with the image slice of the first stack. The rotation angle associated with the image slice of the first stack may relate to a distance (e.g., a length of a portion of the first couch) between the reference position to the specific first position reflected in the image slice of the first stack.

The longer a length of a portion of the first couch between the reference position to a specific first position is, the greater the rotation angle associated with the specific first position may be. In some embodiments, the rotation angle associated with the specific first position may be determined based on the length of the portion of the first couch between the reference position to the specific first position, an offset in a vertical direction of the first couch at the specific first position of the first conformation with respect to the second conformation, and/or a distance in a horizontal direction between the reference position and the specific first position. More descriptions for determining a displacement component associated with a specific position may be found in FIG. 8 and/or FIG. 9.

In 1008, the first stack of image slices may be adjusted based on the displacement field. Operation 1008 may be performed by the image correction module 530. In some embodiments, the first stack of image slices may be adjusted by moving all pixels in at least one image slice in the first stack based on a corresponding displacement component. In some embodiments, the first stack of image slices may correspond to a volume image (e.g., a three-dimension image) relating to the ROI. The first stack of image slices may be adjusted by moving all voxels in the volume image corresponding to the first stack of image slices based on the displacement field. In some embodiments, the first stack of images may correspond to imaging data relating to the ROI. The imaging data relating to the ROI may be represented by spatial basis function representations. The imaging data relating to the ROI may be adjusted by adjusting the spatial basis function representations. Then, the adjusted first stack of image slices may be obtained based on the adjusted imaging data.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 1002 may be omitted. As another example, operations 1002 and 1004 may be performed simultaneously. In some embodiments, operation 1008 may be omitted. For example, an image slice in the first stack corresponding to the reference position of the first couch does not need to be adjusted based on a displacement component associated with the reference position.

Examples

The following examples are provided for illustration purposes, and not intended to limit the scope of the present disclosure.

Figure 11A:
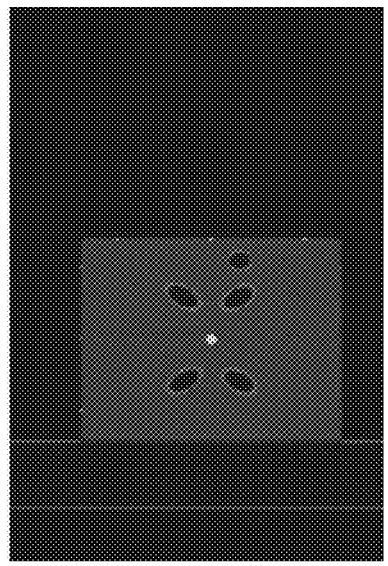
FIGS. 11A-11C are images affording sagittal views relating to an exemplary phantom and a couch supporting the phantom according to some embodiments of the present disclosure.
Figure 11C:
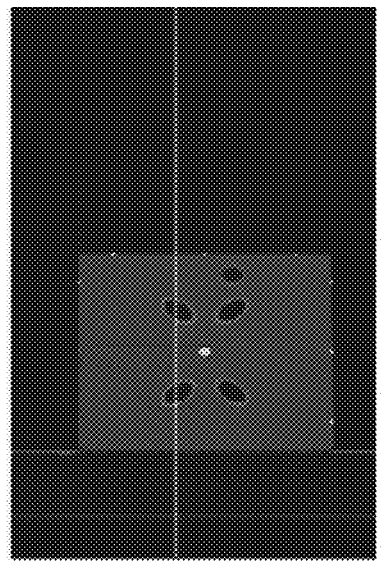
Figure 11B:
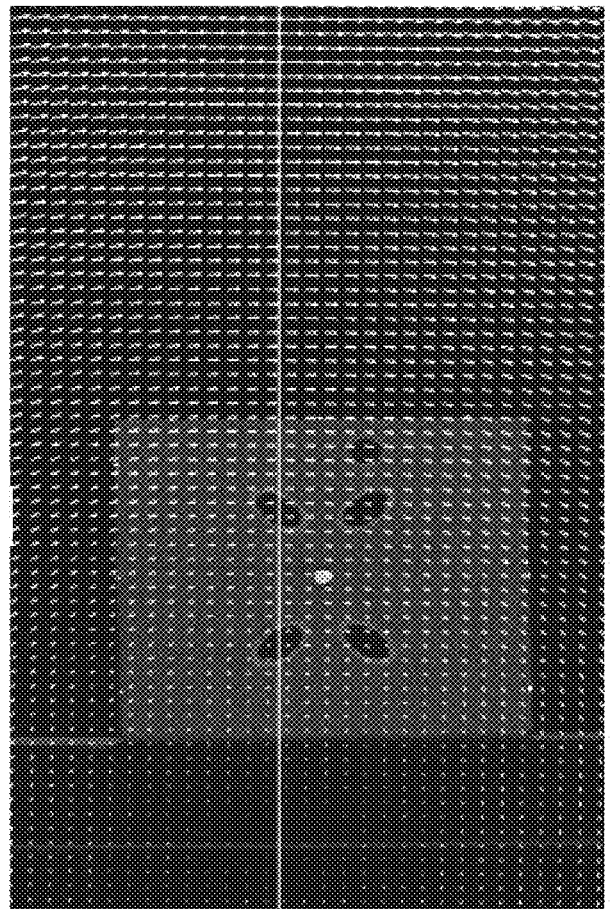

FIGS. 11A-11C are images affording sagittal views relating to an exemplary phantom and a couch supporting the phantom according to some embodiments of the present disclosure. A first image shown in FIG. 11A relates to a phantom with negligible weight and a couch supporting the phantom. A second image shown in FIG. 11B relates to the phantom with weight of 100 kilograms and the couch supporting the phantom. A displacement field including a plurality of displacement components as described elsewhere in the present disclosure is shown in FIG. 11B as white arrows. More descriptions of the white arrows may be found in FIG. 12B. The third image shown in FIG. 11C was obtained by correcting the second image based on the displacement field in the second image.

Figure 12A:
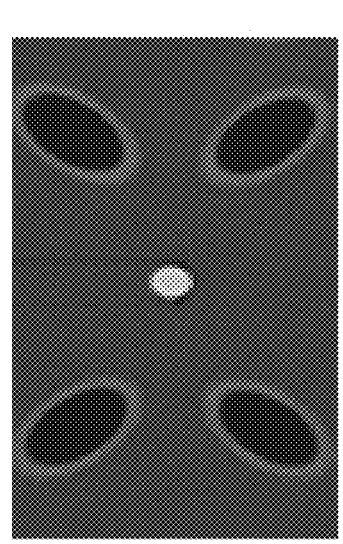
FIGS. 12A-12C are images relating to the same locally amplified region in FIGS. 11A-11C according to some embodiments of the present disclosure.
Figure 12C:
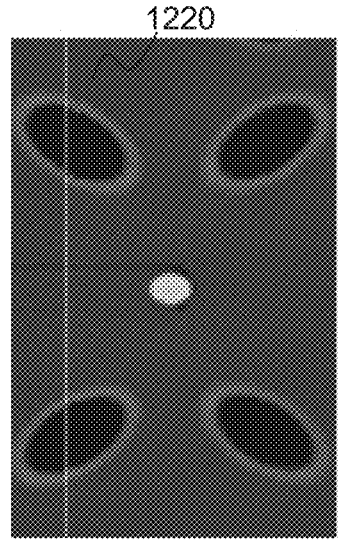
Figure 12B:
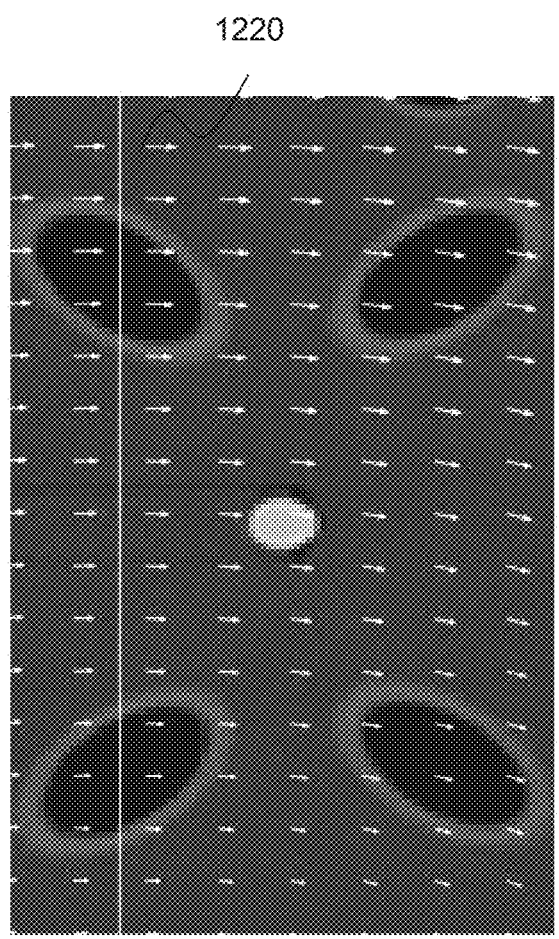

FIGS. 12A-12C are images relating to the same locally amplified region in FIGS. 11A-11C according to some embodiments of the present disclosure. As shown in FIG. 12B, white arrows denote a displacement field. The displacement field includes a plurality of local displacement components as described elsewhere in the present disclosure. Each of the plurality of displacement components is denoted by a white arrow. The displacement components correspond to multiple positions of the couch. A line 1220 in FIG. 12B or in FIG. 12C denotes a reference axial view corresponding to a reference position of the couch as described elsewhere in the present disclosure. The displacement component corresponding to a position of the couch far from the reference axial view is greater than that corresponding to a position of the couch close to the reference axial view.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques.

Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on a computing device having at least one processor and at least one computer-readable storage medium, the method comprising:
   obtaining a first set of imaging data relating to a subject and a first couch supporting the subject, the first couch having a plurality of first positions reflected in the first set of imaging data as a first conformation;
   determining an intersection between a reference conformation and the first conformation; and
   determining, based on the intersection between the reference conformation and the first conformation, the first conformation, and the reference conformation, a displacement field associated with the first set of imaging data with respect to the reference conformation, the displacement field including a plurality of displacement components corresponding to the plurality of first positions.

2. The method of claim 1, wherein the determining, based on the intersection between the reference conformation and the first conformation, the first conformation, and the reference conformation, a displacement field associated with the first set of imaging data with respect to the reference conformation includes:
   for one first position of the first couch,
   determining a corrected first point on the reference conformation corresponding to a first point of the first set of imaging data on the first conformation based on the intersection, the first point corresponding to the one first position of the first couch; and
   determining a displacement component associated with the first point, wherein the displacement component of the first point is determined as a vector from the first point to the corrected first point.

3. The method of claim 2, wherein a first distance between the corrected first point and the intersection equals to a second distance between the first point and the intersection.

4. The method of claim 2, wherein the displacement component of the first point includes a third distance from the first point to the corrected first point, and a direction from the first point to the corrected first point.

5. The method of claim 2, wherein distances between various first points and the intersection change as a function of corresponding first positions nonlinearly.

6. The method of claim 1, further comprising:
adjusting, based on the displacement field, the first set of imaging data with respect to the reference conformation; and
obtaining, based on the adjusted first set of imaging data, an image of the subject with respect to the reference conformation.

7. The method of claim 6, wherein the adjusting, based on the displacement field, the first set of imaging data with respect to the reference conformation includes:
adjusting imaging data in an axial view corresponding to the first point in a sagittal view based on the displacement component corresponding to the first point.

8. The method of claim 7, further comprising:
generating an adjusted 3D image slice or an adjusted 2D image slice in a view other than the axial view based on the adjusted imaging data.

9. The method of claim 6, wherein the adjusting, based on the displacement field, the first set of imaging data with respect to the reference conformation includes:
moving, based on the displacement field, spatial basis function representations corresponding to the first set of imaging data.

10. The method of claim 1, wherein the displacement field includes a plurality of rotation angles, and the plurality of rotation angles relate to spatial basis function representations corresponding to the first set of imaging data.

11. The method of claim 10, further comprising:
determining a reference position of the first couch reflected in the first set of imaging data, the first conformation of the first couch coinciding with the reference conformation at the reference position, the reference position corresponding to a reference spatial basis function representation.

12. The method of claim 1, wherein the reference conformation includes a straight horizontal line.

13. The method of claim 1, wherein the reference conformation corresponds to a plurality of second positions reflected in a second set of imaging data.

14. The method of claim 13, wherein the second set of imaging data afford a sagittal view relating to the subject and a second couch supporting the subject, and the plurality of second positions correspond to the second couch.

15. A method implemented on a computing device having at least one processor and at least one computer-readable storage medium, the method comprising: obtaining a stack of image slices affording axial views relating to a subject or a region of interest (ROI) of the subject and a first couch supporting the subject, the first couch having a plurality of first positions reflected in the stack of image slices as a first conformation; determining an intersection between a reference conformation and the first conformation; determining, based on the intersection between the reference conformation and the first conformation, the first conformation, and the conformation, a displacement field associated with the stack of image slices with respect to the reference conformation, the displacement field including a plurality of displacement components corresponding to the plurality of first positions, and each image slice of the stack corresponding to one displacement component of the plurality of displacement components.

16. The method of claim 15, further comprising:
adjusting, based on the displacement field, spatial basis function representations corresponding to imaging data, wherein the imaging data corresponds to the stack of image slices.

17. The method of claim 15, further comprising:
adjusting, based on the displacement field, the stack of image slices.

18. The method of claim 15, wherein the first conformation corresponds to a plurality of first positions of a first couch reflected in the stack of image slices, and the reference conformation corresponds to a plurality of second positions of a second couch reflected in an image slice affording a sagittal view.

19. The method of claim 18, wherein the stack of image slices are acquired by a first device and the image slice is acquired by a second device different from the first device.

20. A method implemented on a computing device having at least one processor and at least one computer-readable storage medium, the method comprising:
obtaining a first image slice in a first view relating to a subject or a region of interest (ROI) of the subject and a first conformation, the first image slice corresponding to a stack of second image slices in a second view; and
determining an intersection between a reference conformation and the first conformation;
determining, based on the intersection between the reference conformation and the first conformation, the first conformation, and the reference conformation, a displacement field associated with the first image slice with respect to the reference conformation, the displacement field including a plurality of displacement components, and each second image slice of the stack corresponding to one displacement component of the plurality of displacement components.

* * * * *